US010822611B2

(12) United States Patent
Arimura et al.

(10) Patent No.: US 10,822,611 B2
(45) Date of Patent: Nov. 3, 2020

(54) METHOD FOR EDITING PLANT MITOCHONDRIAL GENOME

(71) Applicant: The University of Tokyo, Tokyo (JP)

(72) Inventors: Shin-ichi Arimura, Tokyo (JP); Nobuhiro Tsutsumi, Tokyo (JP); Kenta Katayama, Tokyo (JP); Tomomi Hidaka, Tokyo (JP); Tomohiko Kazama, Sendai (JP); Kinya Toriyama, Sendai (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 185 days.

(21) Appl. No.: 15/895,118

(22) Filed: Feb. 13, 2018

(65) Prior Publication Data

US 2018/0230477 A1    Aug. 16, 2018

(30) Foreign Application Priority Data

Feb. 14, 2017    (JP) ................. 2017-024923

(51) Int. Cl.
*C12N 15/82*    (2006.01)
*C12N 15/79*    (2006.01)
*C12N 15/10*    (2006.01)

(52) U.S. Cl.
CPC ....... *C12N 15/8213* (2013.01); *C12N 15/102* (2013.01); *C12N 15/79* (2013.01); *C12N 15/8289* (2013.01)

(58) Field of Classification Search
None
See application file for complete search history.

(56) References Cited

FOREIGN PATENT DOCUMENTS

| JP | 2016-521561 A1 | 7/2016 |
| WO | 2014/199358 A1 | 12/2014 |

OTHER PUBLICATIONS

Davila et al. (2011) BMC Biol 9:64.*
Miller-Messman et al. (2012) Plant Physiol 159:211-26.*
Bacman et al. (2013) Nat Med 19(9):1111-13.*
Niazi et al. (2013) Mitochondrion 13:548-58.*
Quétier (2016) Plant Sci 242:65-76.*
Chen & Gao (2013) J Genet Genomics 40, 271-279.*
Kazama et al. (2019) Nat Plants 5:722-30.*
Huang et al. (2009) Plant Physiol 150:1272-85.*
Larosa, V. et al., "Transformation of the mitochondrial genome",The International Journal of Development Biology, 2013, pp. 659-665; described in the Specification.
Gualberto, J. M. et al.,"The Plant Mitochondrial Genome: Dynamics and Maintenance", Biochimie 100, 2014, pp. 107-120; described in the Specification.
Kubo, T. et al.,"Angiosperm Mitochondrial Genomes and Mutations", Mitochondrion 8, 2008, pp. 5-14; described in the Specification.
Skippington, E. et al, "Miniaturized mitogenome of the parasitic plant *Viscum scurruloideum* is extremely divergent and dynamic and has lost all nad genes", Proc Natl Acad Sci USA, 2015, pp. E3515-E3524; described in the Specification.
Sloan, D. B. et al., "Intraspecific Variation in Mitochondrial Genome Sequence, Structure, and Gene Content in Silene vulgaris, an Angiosperm with Pervasive Cytoplasmic Male Sterility", New Phytologist, 2012, pp. 1228-1239; described in the Specification.
Davila, J. I. et al. "Double-strand Break Repair Processes Drive Evolution of the Mitochondrial Genome in *Arabidopsis*", BMC Biology, 2011, 9:64; described in the Specification.
Miller-Messmer, M. et al., "RecA-Dependent DNA Repair Results in Increased Heteroplasmy of the *Arabidopsis* Mitochondrial Genome", Plant Physiology , May 2012, vol. 159, pp. 211-226; described in the Specification.
Cappadocia, L. et al, "Crystal Structures of DNA-Whirly Complexes and Their Role in *Arabidopsis* Organelle Genome Repair", The Plant Cell, Jun. 2010, vol. 22, pp. 1849-1867; described in the Specification.
Bacman, S. R. et al., "Specific Elimination of Mutant Mitochondrial Genomes in Patient-derived Cells by mitoTALENs" Nat Med., Sep. 2013, pp. 1-13; described in the Specification.
Reddy, P. et al., "Selective Elimination of Mitochondrial Mutations in the Germline by Genome Editing", Cell 161, Apr. 23, 2015, pp. 459-469; described in the Specification.
Iwabuchi, M. et al., "Processing followed by complete editing of an altered mitochondrial atp6 RNA restores fertility of cytoplasmic male sterile rice", The EMBO Journal, 1993, vol. 12, No. 4, pp. 1437-1446; described in the Specification.
Kazama, T. et al., "Suppression Mechanism of Mitochondrial ORF79 Accumulation by Rf1 Protein in BT-type Cytoplasmic Male Sterile Rice", The Plant Journal, 2008, pp. 619-628; described in the Specification.
Wang, Z. et al., "Cytoplasmic Male Sterility of Rice with Boro II Cytoplasm Is Caused by a Cytotoxic Peptide and Is Restored by Two Related PPR Motif Genes via Distinct Modes of mRNA Silencing", The Plant Cell, Mar. 2006, vol. 18, pp. 676-687; described in the Specification.

(Continued)

*Primary Examiner* — Russell T Boggs
(74) *Attorney, Agent, or Firm* — Westerman, Hattori, Daniels & Adrian, LLP

(57) ABSTRACT

A method for inducing a structural change in a plant mitochondrial genome is provided. The invention relates to a method for inducing a structural change in a mitochondrial genome in a plant cell by introducing a double-strand break into a target sequence region on mitochondrial genomic DNA in a plant cell, which is present in individual molecule species of the mitochondrial genomic DNA. In addition, the present invention also relates to a method for deleting a gene that is present in mitochondrial genomic DNA in a plant cell by introducing a double-strand break into the gene or a region near the gene, which is present in individual molecule species of the mitochondrial genomic DNA. Moreover, the invention also relates to a plant cell having a mitochondrial genome, in which a structural change has been induced by the method, and a seed and a plant having the plant cell.

7 Claims, 13 Drawing Sheets

Specification includes a Sequence Listing.

(56) References Cited

OTHER PUBLICATIONS

Akimura, S. "Technique of artificially modifying plant mitochondrial genome and production of male sterile plants", Symposium Abstract published on Oct. 3, 2016; with English translation of important part. (2 pages).

Arimura, S., "Technique of artificially modifying plant mitochondrial genome and production of male sterile plants", Symposium, Published on Oct. 4, 2016, with English translation. (60 pages).

Arimura, S., "Technique of artificially modifying plant mitochondrial genome and production of male sterile plants", Research Report published on Jan. 31, 2017, with English translation of important parts. (12 pages).

Arimura, S., "Technique of artificially modifying plant mitochondrial genome and production of male sterile plants", Biomass Expo 2016, Published on Jun. 15, 2016; with English translation of important parts. (2 pages).

* cited by examiner (SEQ ID NO 78)

(SEQ ID NO 79)
(SEQ ID NO 80)
(SEQ ID NO 81)

Fig. 5

|  | Lines | Types | Edge 1 | Length (bp) | Edge 2 |
|---|---|---|---|---|---|
| hr1 | #2-1, #3-2, #3-5 | IR(IR07) | sub2 126,523 + | 167 | sub2 208,501 + |
| hr2 | #2-5 | short | sub2 128,651 + | 26 | sub2 192,520 +, sub2 319,949 +, sub2 439,084 + |
| hr3 | #3-4 | IR(IR35) | sub2 128,739 + | 69 | sub1 68,748 − |
| hr4 | #3-9 | short | sub2 131,408 + | 13 | sub2 115,480 − |
| hr5 | #2-4, #3-3, #3-8 | short | sub2 131,647 + | 44 | sub2 222,730 + |
| hr6 | #3-6 | short | sub2 131,695 + | 47 | sub2 99,023 + |
| hr7 | #2-2, #2-7, #3-10 | short | sub2 132,640 + | 25 | sub2 202,408 + |
| hr8 | #2-3 | short | sub2 132,675 + | 18 | sub2 202,868 + |
| hr9 | #3-1 | short | sub2 133,118 + | 27 | sub2 99,929 − |
| hr10 | #3-11 | short | sub2 133,187 + | 11 | sub1 62,765 + |
| hr11 | #3-11 | short | sub2 133,492 − | 30 | sub2 204,521 − |

Mitochondrial localization signal-added tandem construct

Constantly high expression tandem construct

Estrogen-induced expression tandem construct

METHOD FOR EDITING PLANT MITOCHONDRIAL GENOME

BACKGROUND OF THE INVENTION

Field of the Invention

The present invention relates to a method for editing or modifying a plant mitochondrial genome.

Description of the Related Art

A technique of transforming the nuclear genome and chloroplast genome of plants has been established over a quarter of a century ago, and an enormous amount of analysis and basic understanding have been achieved. On the other hand, it has not yet been reported that a mitochondrial genome transformant has been successfully produced using organisms other than unicellular organisms such as yeast or green alga *Chlamydomonas* (Non Patent Literature 1).

Nuclear genome is generally a diploid having 2 copies of genome sets. On other hand, mitochondrial genome is present in an amount of several tens to several hundreds of copies in a cell. Moreover, the mitochondrial genome of seed plants (50 kb to >10 Mb) is much larger than that of mammals (15 to 20 kb) in size, and it includes a large number of repeated sequences. It is considered that a variety of chimeric ORFs are generated as a result of homologous recombination (Non Patent Literatures 2 to 5), and thus that the mitochondrial genome of plants is present in a state in which genomic DNA molecule species having different sizes are mixed (multipartite structure).

Repeated sequences are scattered in the mitochondrial genomic DNA of plants. Among such repeated sequences, homologous recombination takes place between repeated sequences having a particularly long size (from several kb), so that a plurality of interconvertible genomic structures are formed. In addition, such homologous recombination also takes place between repeated sequences having an intermediate size (intermediate size repeats; ISRs) (generally, 50 to 600 bp), and it is considered that this homologous recombination would induce complicated genome rearrangement. However, in general, the frequency of the homologous recombination of ISRs is extremely low. It is considered that recombination involving ISRs would be mostly associated with a DNA break-induced replication (BIR) pathway (Non Patent Literature 6), a pathway mediated by single-strand annealing (SSA) (Non Patent Literature 7), etc. Such a low-frequency recombination activity is non-allelic, the process thereof is non-uniform, and only either one of predicted reciprocal recombination products is generated. Moreover, it has also been reported that illegitimate recombination, which is associated with the homology of a very short nucleotide sequence consisting of several nucleotides, takes place (Non Patent Literature 8).

Furthermore, when mitochondrial genomic DNA is damaged, a repair mechanism functions, as in the case of nuclear genomic DNA. In general, when double-strand breaks (DSBs) are induced to mitochondrial genomic DNA by a drug or the like, repair is carried out by homologous recombination, and RecA is involved in the formation of D-loop generated in the initial process thereof. It has been reported that if such RecA-dependent mitochondrial DNA repair is hindered by the mutation of RecA or the like, products as a result of microhomology-mediated recombination (MHMR), which is caused by DSBs introduced into mitochondrial DNA, are accumulated (Non Patent Literature 2). There are several mitochondrial genomic DNA repair pathways, and it is considered that each repair pathway functions depending on circumstances. However, according to the previous reports, DSB has taken place randomly, the position of DSB has been unknown, and it has been assumed that such DSB had taken place very near to the site in which a repair sequence has been found. Further, DSBs and repair products have been accumulated only in some DNA molecule species in a cell, and thus, normal sequences and repaired sequences have been mixed in the cell (heteroplasmy), and therefore, unification of the genome to the repaired sequence (homoplasmy) has not yet been achieved (Non Patent Literatures 2, 6, 7 and 8).

By the way, the plant mitochondrial genome comprises not only genes that are also present in the animal mitochondrial genome, such as genes encoding the subunits of electron transport system-associated complexes and ribosome proteins, but also genes that are specific to plants, such as a gene associated with cytoplasmic male sterility (CMS). CMS is a common phenotype that is used to harvest F1 seeds in F1 breeding which utilizes a hybrid vigor phenomenon. If seeds are harvested as a result of breeding with CMS individuals, F1 seeds can be certainly obtained without performing an emasculation, etc. However, at present, CMS has been problematic in terms of genetic vulnerability caused by a few types thereof or difficulty in the development thereof, and thus, it has been desired to establish a novel method for creating CMS. If the mitochondrial genome of crops could be directly modified and CMS could be imparted thereto, a variety of CMSs would be imparted to a variety of crops and varieties, so that such CMSs could be promptly introduced therein without disturbing the nucleus or the chloroplast genomic sequence, thereby greatly contributing to increased production of crops, stable production, etc.

However, as described above, the mitochondrial genome of plants has a more complicated structure than that of animals, and such complicity becomes one of factors for retarding the development of a method for analyzing and editing a plant mitochondrial genome.

There have been several reports regarding artificial modification of the mitochondrial genome of animals (Non Patent Literature 9 and Non Patent Literature 10). Bacman et al. have introduced a double-strand break into the mutation site on mitochondrial DNA, which causes mitochondrial disease, by using TALENs designed for use in mitochondria (transcription activator-like effector nucleases, which is hereinafter referred to as "mito-TALENs"), and as a result, they have demonstrated that mitochondrial DNA molecule species having mutation have disappeared (Non Patent Literature 9). Meanwhile, Reddy et al. have cleaved a human mitochondria mutation site, which causes Leber's hereditary optic neuropathy (LHOND) and NARP (Neurogenic muscle weakness, Ataxia, and Retinitis Pigmentosa), by using mito-TALENs, and as a result, they have succeeded in reducing mutated mitochondrial DNA molecule species (Non Patent Literature 10).

These reports demonstrate that when a specific site of animal mitochondrial DNA is cleaved with mito-TALENs, mitochondrial DNA molecule species having the cleaved target site disappears without being repaired. However, these reports do not state whether such mito-TALENs are able to induce a change in the phenotype due to gene-specific editing and the disappearance of only the target gene, such as deletion of only the target gene.

Still further, regarding the nuclear genomic DNA of plants, it has been reported that when a double-strand break is introduced into the nuclear genomic DNA by using TALENs, it is repaired by non-homologous end joining (NHEJ) (Patent Literature 1). Patent Literature 1 discloses that a double-strand break can also be introduced into DNA in the chloroplast or mitochondria by the same method as described above. However, this publication does not describe at all the subsequent influence of the introduction of the double-strand break on the chloroplastic and mitochondrial genomic DNA. That is to say, this publication describes that NHEJ is induced when one or more double-strand breaks are introduced into the nuclear genomic DNA of plants, but the case of the mitochondrial genomic DNA of plants is unknown.

CITATION LIST

Patent Literature

Patent Literature 1: JP Patent Publication (Kohyo) No. 2016-521561 A

Non Patent Literature

Non Patent Literature 1: Larosa et al., Int J Dev Biol 57, 659-665, 2013
Non Patent Literature 2: Gualberto et al., Biochimie 100, 107-120, 2014
Non Patent Literature 3: Kubo et al., Mitochondrion 8, 5-14, 2008
Non Patent Literature 4: Skippington et al., Proc Natl Acad Sci USA 112, E3515-3524, 2015
Non Patent Literature 5: Sloan et al., New Phytol 196, 1228-1239, 2012
Non Patent Literature 6: Davila et al., BMC Biol. 9, 64, 2011
Non Patent Literature 7: Miller-Messmer et al., Plant Physiol. 159, 211-226, 2012
Non Patent Literature 8: Cappadocia et al., Plant Cell 22, 1849-1867, 2010
Non Patent Literature 9: Bacman et al., Nat Med 19, 1111-1113, 2013
Non Patent Literature 10: Reddy et al., Cell 161, 459-469, 2015
Non Patent Literature 11: Iwabuchi et al., EMBO J 12, 1437-1446, 1993
Non Patent Literature 12: Kazama et al., Plant J 55, 619-628, 2008
Non Patent Literature 13: Wang et al., Plant Cell 18, 676-687, 2006

SUMMARY OF THE INVENTION

Problems to be Solved by the Invention

In consideration of the aforementioned circumstances, it is an object of the present invention to provide a method for editing or modifying a mitochondrial genome in a plant. More specifically, it is an object of the present invention to provide a method for inducing a structural change in a plant mitochondrial genome (individual molecule species of plant mitochondrial genomic DNAs).

Means for Solving the Problems

The present inventors have targeted orf79 (Non Patent Literatures 10 to 13) of rice, which is a CMS-related gene, and have introduced a double-strand break into genomic DNA in this region, so as to attempt to edit (or modify) orf79. For such a double-strand break introduced into the genomic DNA, TALENs (transcription activator-like effector nucleases) which had been designed for mitochondria (mito-TALENs) were used.

In this study, the present inventors have allowed mito-TALENs to express in 18 strains of rice plants, while targeting orf79. As a result, differing from the example of the nuclear genome of plants (i.e., repair takes place by NHEJ), it was confirmed that orf79 was destroyed (deleted) in the 16 strains. Upon designing mito-TALENs for use in plants, attention should be paid to the point that if a mitochondrial localization signal peptide derived from organisms other than plants is directly used to transfer TALENs into plant mitochondria, the TALENs are also transferred into chloroplasts. Thus, the inventors have used a plant-derived mitochondrial localization peptide as a signal peptide for transferring TALENs into plant mitochondria. As a result, mito-TALENs could be efficiently transferred into plant mitochondria.

Specifically, as a result of the introduction of a double-strand break into orf79 as a target (which is an introduction of a double-strand break into orf79 as a target, wherein the orf79 is present in all molecule species of plant mitochondrial genomic DNAs, so that such a double-strand break is introduced into almost all mitochondrial genomic DNAs present in a cell), a large deletion/disappearance of several hundreds of bp to several kb took place in the orf79 region. On the other hand, almost all other genes or ORFs were maintained. These results were greatly different from the case of introducing a double-strand break into the nuclear genome of a plant (in which a deletion/insertion of approximately several bp takes place as a result of NHEJ repair; Patent Literature 1). In the case of plant mitochondrial DNA, introduction of a double-strand break in the mitochondrial DNA resulted in disappearance of a portion of mitochondrial DNA, unlike in the case of animal mitochondrial DNA.

That is to say, the present inventors have found that, when a double-strand break is introduced into the same sequence region (i.e., the orf79 region in the Examples) in the entire plant mitochondrial genomic DNA molecule species, an illegitimate homologous recombination (HR) is induced, mediated by a relatively short homologous sequence, between a sequence that is present near the cleavage region and a sequence that is present in another region, and as a result, a large deletion/disappearance takes place in a mitochondrial genomic region near the double-strand break site.

The above-described results, which were revealed by the present inventors, were unpredictable from the results obtained by introducing a double-strand break into animal mitochondrial genomic DNA or plant nuclear genomic DNA by TALENs.

Moreover, since several hundreds of copies of plant mitochondrial genomes are present in a single cell, if gene disruption takes place in some copies, it is likely to cause problems regarding mixing with normal genes (heteroplasmy). However, as a result of a sequence analysis performed after the gene disruption, only DNA sequences comprising a deletion of orf79 were found and wild-type DNA sequences were not found (see the results from Examples and FIGS. 2A, 2B, 3A, 3B, 4A, 4B, 6A and 6B). Accordingly, it is considered that a majority of strains comprising disruption of orf79 are unified to gene disruption-type strains (homoplasmy).

The present invention has been completed based on the aforementioned findings.

Specifically, the present invention includes the following (1) to (18):

(1) A method for inducing a structural change in a mitochondrial genome in a plant cell by introducing a double-strand break into a target sequence region present in individual mitochondrial genomic DNA molecule species in the plant cell.

(2) The method according to the above (1), wherein the structural change in the mitochondrial genome is induced by DNA recombination occurring between a sequence that is present near the target sequence region and a homologous sequence thereof that is present in another region.

(3) A method for deleting a gene that is present in individual mitochondrial genomic DNA molecule species in a plant cell by introducing a double-strand break into the gene or a region near the gene.

(4) The method according to the above (3), wherein the deletion of the gene is induced by DNA recombination occurring between the gene or a sequence that is present in a region near the gene and a homologous sequence that is present in another region.

(5) The method according to the above (3) or (4), wherein the gene is a gene responsible for male sterility.

(6) The method according to any one of the above (1) to (5), wherein the double-strand break is introduced by TALEN (transcription activator-like effector nucleases).

(7) The method according to the above (6), wherein a mitochondrial localization signal peptide derived from a protein localized in plant mitochondria is used to transfer the TALEN into mitochondria.

(8) The method according to the above (7), wherein an expression construct of the TALEN is prepared by a method comprising the following steps (a) to (c):

(a) a step of providing an entry vector 1, in which a TALEN left is inserted between two homologous recombination sequences L1 and L4, an entry vector 2, in which a terminator, a promoter and a mitochondrial localization signal are inserted in this order between two homologous recombination sequences R4 and R3, and an entry vector 3, in which a TALEN right is inserted between two homologous recombination sequences L3 and L2;

(b) a step of providing a destination vector, into which a promoter, a mitochondrial localization signal, a homologous recombination sequence R1 and a homologous recombination sequence R2 are inserted in this order; and (c) a step of mixing the entry vector 1, the entry vector 2, the entry vector 3 and the destination vector with one another, so that homologous recombination is allowed to take place between L1 and R1, between L4 and R4, between L3 and R3, and between L2 and R2.

(9) A plant cell having a mitochondrial genome, in which a structural change has been induced by the method according to the above (1), (2), (6), (7) or (8).

(10) A seed or a plant comprising the plant cell according to the above (9).

(11) A plant cytoplasm having a mitochondrial genome, in which a structural change has been induced by the method according to the above (1), (2), (6), (7) or (8).

(12) Mitochondria having a mitochondrial genome, in which a structural change has been induced by the method according to the above (1), (2), (6), (7) or (8).

(13) A mitochondrial genome, in which a structural change has been induced by the method according to the above (1), (2), (6), (7) or (8).

(14) A plant cell having a mitochondrial genome, in which at least one gene has been deleted by the method according to any one of the above (3) to (8).

(15) A seed or a plant comprising the plant cell according to the above (14).

(16) A plant cytoplasm having a mitochondrial genome, in which at least one gene has been deleted by the method according to any one of the above (3) to (8).

(17) Mitochondria having a mitochondrial genome, in which at least one gene has been deleted by the method according to any one of the above (3) to (8).

(18) A mitochondrial genome, in which at least one gene has been deleted by the method according to any one of the above (3) to (8).

Advantageous Effects of the Invention

According to the method of the present invention, a structural change can be induced in a plant mitochondrial genome.

According to the method of the present invention, it is possible to carry out gene disruption that targets a gene existing on a plant mitochondrial genome, and to create a novel chimeric gene.

BRIEF DESCRIPTION OF THE DRAWINGS

FIG. 1A: Mitochondrial localization signal (MLS)-fused TALENs (TAL), namely, mito TALENs (TALEN-Left and TALEN-Right) are expressed from T-DNA inserted into the nuclear genome, and are then imported into mitochondria. FIG. 1B: A tumor-inducing plasmid (Ti-DNA) with an expression cassette of mito-TALEN is schematically shown. FIG. 1C: Genomic structures and a nucleotide sequence around orf79 with target sites of mito TALEN2 and mito TALEN3 are shown.

FIG. 2A: The results of PCR analysis of orf79 are shown. The positions of PCR primers are shown in FIG. 1C (arrows under nucleotides). T65; non-CMS rice Taichung 65, DDW; double distilled water, and cox 2; non-target gene on the mitochondrial genome. FIG. 2B: The results of southern blot analysis of atp6 and orf79 are shown. Total DNA was digested with EcoRI.

FIG. 3A: Genomic structure near orf79 is shown (top). The PCR regions amplified in FIG. 3B (i to x), repeat structures (LR02-1 and IRs), and the remaining/deletion region of each transformant (bottom) are shown. The solid line indicates an existing region, <hrN> indicates a homologous recombination site, and the broken line indicates an LR02-1 region. FIG. 3B: The results of PCR analysis around orf79 in transformant are shown.

FIG. 4A: The left view shows the results of Southern blot analysis, whereas the right view schematically shows the state of homologous recombination with a hr1 sequence. Moreover, EcoRI sites (E1 to E5) and probes (wavy lines) are shown. FIG. 4B shows a sequence alignment of the donor, recipient and recombined sequence of hr10.

FIG. 5 shows the positions of homologously recombined regions on the genome. For example, hr1 was detected in the strains #2-1n, #3-2 and #3-5, and a sequence at Edge 1 was connected to Edge 2 via a 167-bp homologous sequence. The symbol "+" (or "−") indicates the direction of the connection.

FIG. 6A shows a region around orf79, and FIG. 6B shows a total mitochondrial genomic region. The schematic view in the upper view shows a genomic structure. The lower part shows a relative read depth (the ratio of the number of sequences read of each plant to the number of sequences read of BTA in each position) obtained when the total DNA of each plant is decoded using a next-generation sequencer and is then mapped. The asterisk shows a deleted portion other than orf79.

FIG. 7A is a photograph showing self-pollinated strains #3-7 (left; orf79-present) and #3-11 (right; orf79-absenta). FIG. 7B shows the results of male fertility test as the rate (%) of successful self-crossed seed sets in the transformants. The rate of the strains #2-6 and #3-7 was 0%. N=3. The bar indicates a mean value s. d.

In FIG. 10A, by utilizing Multisite Gateway (registered trademark) pro 3.0, a mitochondrial localization signal-added tandem construct construction system was produced. FIG. 10B shows a schematic view of tandem constructs, which were constructed by utilizing the mitochondrial localization signal-added tandem construct construction system, and also by using two types of promoters (a constant expression promoter (p35S) and an induced expression promoter (pLesA)). P: promoter; T: terminator; MLS: mitochondrial localization signal; TALEN left/right: gene sequences of TALEN left/right (Invitrogen; which are composed of a nuclear localization signal, a V5 epitope tag, a TAL DNA-binding domain, and FokI); p35S: CaMV 35S promoter; pLexA: 35S minimal promoter, to the site upstream of which a LexA operator is ligated; HSP: terminator of Heat shock protein 18.2; T35S: 35S terminator; NOS: NOS terminator; and T3A: T3A terminator.

DETAILED DESCRIPTION OF THE PREFERRED EMBODIMENTS

Figure 1A:
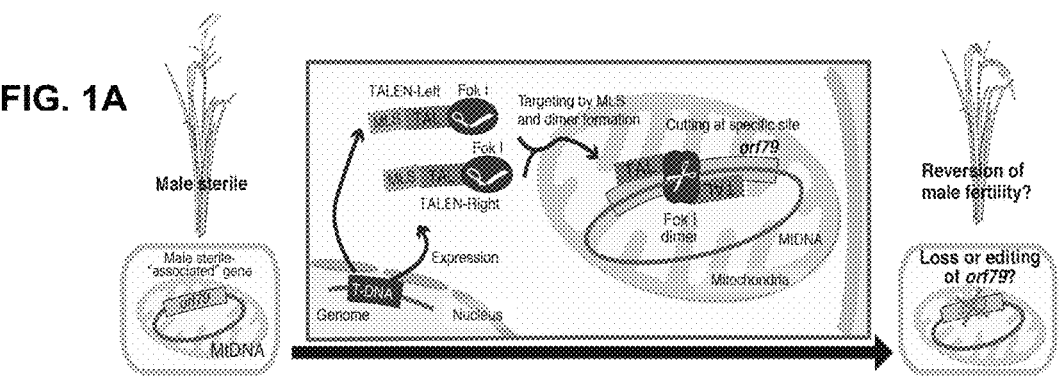
FIGS. 1A to 1C show methods of knocking out mitochondrial orf79, using mito-TALENs.
Figure 1B:
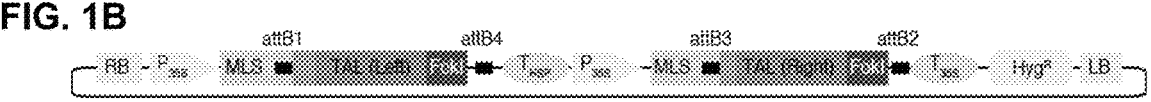

A first embodiment of the present invention relates to a method for inducing a structural change in a mitochondrial genome in a plant cell by introducing a double-strand break into a target sequence region present in individual mitochondrial genomic DNA molecule species in the plant cell.

Herein, the "target sequence region" that is present on mitochondrial genomic DNA means a region, into which a large-scale deletion/disappearance and a rearrangement of a novel genomic DNA sequence are to be induced, or a neighboring region thereof. The "target sequence region" may be any region, as long as it is a sequence region present on mitochondrial genomic DNA. For example, in a case where the presence or absence of such deletion/disappearance and rearrangement of a novel genomic DNA sequence is confirmed, the target sequence region is preferably a region other than essential genes.

Examples of the method for introducing a double-strand break into mitochondrial genomic DNA include a method of using ZFN (Zinc Finger Nucleases) (Urnov et al., Nature 435, 646-651, 2005), a method of using CRISPR-Cas9 (clustered regularly interspaced short palindromic repeats/ CRISPR associated proteins) (Jinek et al., Science 337, 816-821, 2012), a method of using TALEN (transcription activator-like effector nucleases) (Mahfouz et al., Proc Natl Acad Sci USA 108, 2623-2628, 2011), and a method of using various types of restriction enzymes. Among these methods, the method of using TALEN is most preferable.

The number of the "target sequence regions," into which a double-strand break is to be introduced in individual mitochondrial genomic DNA molecule species, is not particularly limited. For example, the number of the target sequence regions is preferably one or more, and more preferably approximately 1 to 5. The degree of introduction of a double-strand break (i.e., the ratio of molecule species, into which a double-strand break has been introduced, to all mitochondrial genomic DNA molecule species in a plant cell) is not particularly limited, as long as the "target sequence region(s)" existing in the plant cell are deleted and almost no target sequence regions are detected. Such degree of introduction of a double-strand break can be easily confirmed by analyzing cleavage conditions according to preliminary experiments. The degree of introduction of a double-strand break is not particularly limited, but the introduction of a double-strand break may be carried out, for example, on preferably 80% or more of, more preferably 90% or more of, and most preferably 95% or more of mitochondrial genomic DNA molecule species having a "target sequence region," which are present in a plant cell. It is to be noted that a deletion of the "target sequence region" can be confirmed by PCR for amplifying the concerned region, Southern blotting using the concerned region as a probe, or the like.

When mitochondrial genomic DNA is cleaved using TALEN, for example, it is necessary to introduce a gene encoding the TALEN into a nuclear genome, and then to transfer the TALEN expressed in the cytoplasm into the mitochondria. An example of the method of introducing TALEN into mitochondria can be a method comprising fusing TALEN with a mitochondrial localization signal peptide (a peptide characterized in that basic amino acids and multiple hydrophobic amino acids alternately appear) and thus allowing the TALEN to express. In order to prevent TALEN from being transferred to the chloroplast, the mitochondrial localization signal peptide that can be used in the embodiment of the present invention is preferably a signal peptide possessed by a protein localized in plant mitochondria. The preferred signal peptide is not limited, but examples of the signal peptide include a signal peptide derived from the ATPase δ' subunit of *Arabidopsis thaliana* (SEQ ID NO: 75), a signal peptide derived from the ALDH2a gene product of rice (SEQ ID NO: 76), and a signal peptide derived from the cytochrome c oxidase Vb-3 of pea (SEQ ID NO: 77).

Otherwise, a method of directly introducing mRNA encoding a TALEN protein or a TALEN protein itself into a cell (wherein examples of the introduction method include a virus method, a particle gun method, a PEG method, a cell-penetrating peptide method, and a method of directly introducing it into mitochondria using a mitochondria-penetrating peptide) can also be applied.

In order to reliably introduce a double-strand break into mitochondrial genomic DNA, a tandem expression Ti plasmid, in which two TALENs (TALEN left and TALEN right; see FIG. 1A) are simultaneously expressed in a single Ti plasmid, and to which a mitochondrial localization signal is added in order to localize it in mitochondria, can be used (see, for example, Kusano et al., Scientific Reports |6:30234|DOI:10.10.8/srep30234, etc.).

Figure 9:
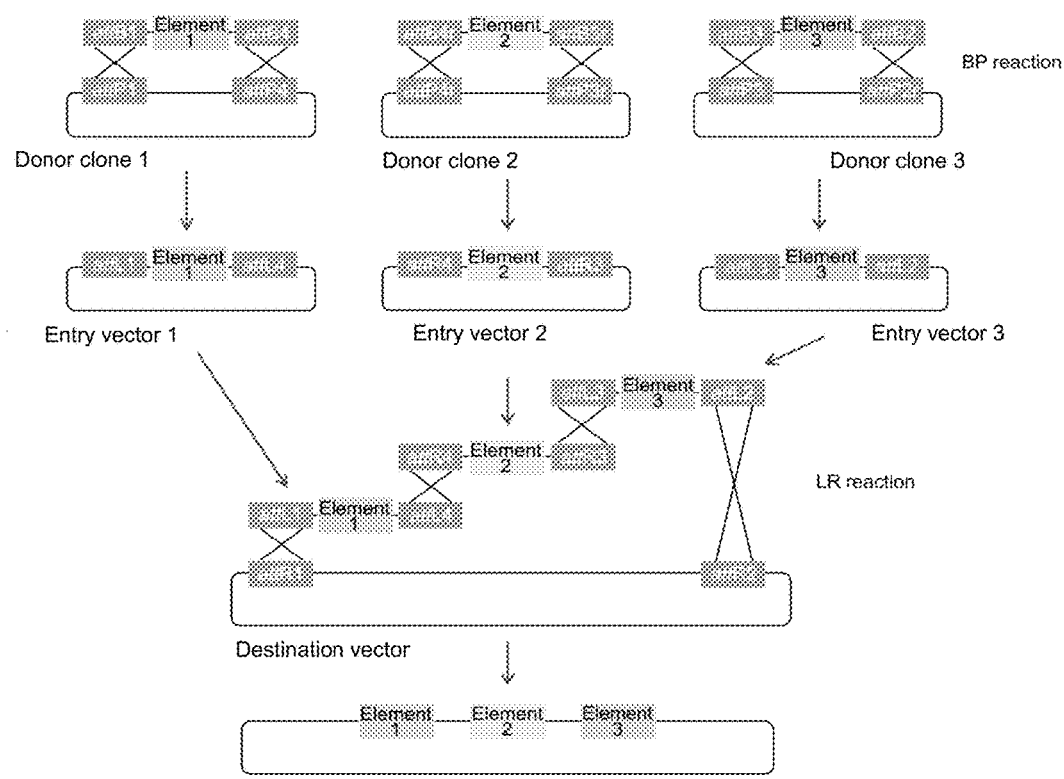
FIG. 9 is an outline of Multisite Gate way.
Figure 10A:
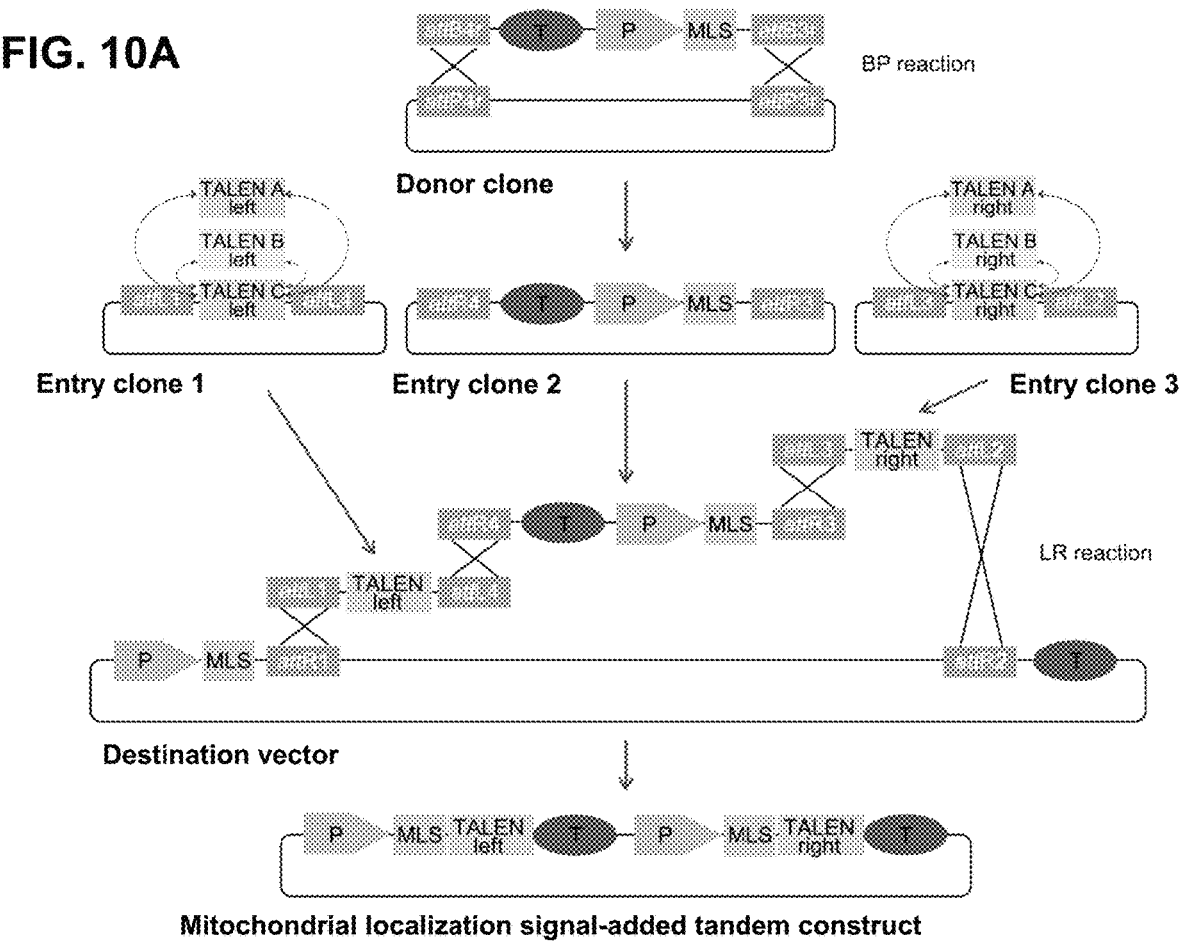
FIGS. 10A and 10B show an outline of the production of a TALEN expression construct.
Figure 10B:
Figure 10B:
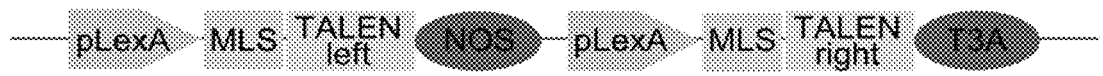

Herein, the present inventors have taken into consideration the fact that it is not easy to clone TALEN because it includes many repeated sequences that are extremely similar to one another. In addition, in order to efficiently carry out a step of producing a large number of plasmids depending on multiple target cleavage regions, the inventors have first produced a system of constructing a mitochondrial localization signal-added tandem construct. Such a system of constructing a mitochondrial localization signal-added tandem construct can be produced, for example, by utilizing MultiSite Gateway (registered trademark) Pro 3.0 (Invitrogen). By using such MultiSite Gateway, a plurality of DNA fragments can be precisely cloned in desired order and direction (FIG. 9). Using this device, the tandem construct construction system can be produced as described below (FIGS. 10A and 10B).

That is to say, a construct, in which mitochondrial localization signal-added TALENs are connected in tandem, can be produced by the following steps (a) to (c) (FIG. 10A):

(a) a step of providing an entry vector 1, in which a TALEN left is inserted between two homologous recombination sequences L1 and L4, an entry vector 2, in which a terminator, a promoter and a mitochondrial localization signal are inserted in this order between two homologous recombination sequences R4 and R3, and an entry vector 3, in which a TALEN right is inserted between two homologous recombination sequences L3 and L2;

(b) a step of providing a destination vector, into which a promoter, a mitochondrial localization signal, a homologous recombination sequence R1 and a homologous recombination sequence R2 are inserted in this order; and (c) a step of mixing the entry vector 1, the entry vector 2, the entry vector 3 and the destination vector with one another, so that homologous recombination is allowed to take place between L1 and R1, between L4 and R4, between L3 and R3, and between L2 and R2.

Needless to say, when a gene is inserted into a vector in each step, such gene insertion is carried out in the correct translational frame, so that mitochondrial localization signal-added TALEN left and TALEN right can be expressed from the construct as a final product. Besides, in each step, as reagents necessary for various types of reactions, which are required to prepare a vector, reagents included with MultiSite Gateway (registered trademark) Pro 3.0 (Invitrogen), etc. can be used. The promoter used herein can be either a constant expression promoter or an induced expression promoter (FIG. 10B). In addition, the expression directions of the two TALENs may be either the same directions or reverse directions.

The above-described tandem construct construction system is extremely useful, in that it is not limited to the case of targeting a mitochondrial genome, but it can also simplify the production of a TALEN expression construct for plants.

The present inventors have discovered for the first time that, when a double-strand break is introduced into individual molecule species of plant mitochondrial genomic DNA, NHEJ repair does not take place, differing from the case of the nucleus, and a recombination takes place between a sequence near the cleavage site and a homologous sequence thereof on mitochondrial genomic DNA, which is apart from the cleavage site. It has been confirmed that chimeric sequences are generated in several sites on the mitochondrial genome as a result of the illegitimate homologous recombination that has occurred between the sequences that have been present apart from each other on the genomic DNA, and that a large-scale rearrangement of the genomic structure has taken place and thus, the structure has changed. The thus confirmed rearrangement of the mitochondrial genomic structure is a phenomenon caused mediated by a homologous sequence between sites that are apart from each other on mitochondrial genomic DNA. Accordingly, it is highly likely that not only the gene or orf present on the mitochondrial genome will disappear due to a change in the genomic structure, but also a DNA sequence having a novel function (i.e., a sequence encoding a protein having a novel function) will be created.

A second embodiment of the present invention relates to a method for deleting a gene that is present in individual mitochondrial genomic DNA molecule species in a plant cell by introducing a double-strand break into the gene or a region near the gene.

As described above, it has been confirmed that when a double-strand break is introduced into plant mitochondrial genomic DNA, the introduced site is not repaired, but a sequence around the cleavage region is connected with a site in a completely different portion on the genome by recombination via a homologous sequence. As a result, a large-scale deletion/disappearance (e.g., a deletion of approximately several hundreds of bp to several kb) occurs, and thereby, the cleavage region, or a gene or orf that is present near the cleavage region is deleted.

That is, by introducing a double-strand break into a desired gene or orf that is present on a plant mitochondrial genome, or near the gene or the orf (preferably, a region within a range of approximately 0 to 10 kb from the gene or orf as a target), the gene or orf can be deleted. The number of double-strand breaks introduced is not particularly limited, as long as it is 1 or greater.

The gene to be deleted is not particularly limited, as long as it is a gene present on a mitochondrial genome. For example, for the purpose of recovering the fertility of a plant, a doublestrand break may be introduced, for example, onto the rice CMS-related gene orf79 (SEQ ID NO: 1) or a neighboring region thereof. The CMS-related genes (orf) of other plants are shown in Table 1 (wherein it is to be noted that Table 1 shows a part extracted from Letian Chen and Yao-Guang Liu, Annu. Rev. Plant Biol. 65, 579-606, 2014).

TABLE 1

| Crop species | CMS type[a] | Associated ORF[b] |
|---|---|---|
| Maize (Zea mays) | CMS-T (S) | urf13-atp4 |
|  | CMS-S (G) | orf355-orf77 |
|  | CMS-C (S) | atp6-C |
| Rice (Oryza sativa) | CMS-BT (G) | B-atp6-orf79 (T) |
|  | CMS-HL (G) | atp6-orfH79 (T) |
|  | CMS-LD (G) | L-atp6-orf79[e] |
|  | CMS-CW (G) | orf307 |
|  | CMS-WA (S) | rpl5-WA352 (T) |
|  | CMS-RT120 | rpl5-orf352 |
|  | CMS-RT98 | orf113-atp4-cox3 |
| Sunflower (Helianthus annuus) | CMS-PET1 (G) | atp1-orf522 |
| Brassica (Brassica napus) | CMS-Ogu (S) | orf138-atp8 |
|  | CMS-Pol (S) | orf224-atp6 |
|  | CMS-Nap (S) | orf222-nad5c-orf139 |

TABLE 1-continued

| Crop species | CMS type[a] | Associated ORF[b] |
|---|---|---|
| Brassica (Brassica juncea) | CMS-Hau (S) | atp6-orf288 (T) |
|  | CMS-orf220 | orf220 (T) |
| Brassica (Brassica tournefortii) | CMS-Tour (S) | atp6-orf263 |
| Radish (Raphanus sativus) | CMS-Kos (S) | orf125-atp8 |
|  | CMS-Don (S) | orf463 |
| Sorghum (Sorghum bicolor) | CMS-A3 (G) | orf107 |
|  | CMS-A1 (G) | unknown |
| Wheat (Triticum aestivum) | CMS-AP | orf256 |
| Common bean (Proteus vulgaris) | CMS-Sprite (S) | atp1-orf98-orf239 (T) |
| Pepper (Capsicum annuum) | CMS-Peterson | cox2-orf456 (T) cox2-orf507 |
| Carrot (Daucus carota) | CMS-Petaloid | orfB |
| Sugar beet (Beta vulgaris) | CMS-Owen | preSatp6 |
|  | I-12CMS(3) | orf129 (T) |
|  | CMS-G | cox2 |

[a]Letters in parentheses indicate the generation where the CMS acts: S, sporophytic; G, gametophytic.
[b]Underlined cotranscripts indicate the CMS-causing open reading frame (ORF); a letter T in parentheses indicates that the biological function as a CMS gene has been validated in Introduction of a double-strand break into a desired gene or a neighboring DNA region thereof can be carried out according to methods of using the aforementioned TALEN, ZFN or CRISPR-Cas9, or methods of using various types of restriction enzymes.

For instance, when the rice CMS-related gene orf79 is deleted using TALENs, a pair of TALENs, namely, TALEN binding to TACCCGAGGGACTAACGGT (SEQ ID NO: 2) in the nucleotide sequence of orf79 and TALEN binding to TCCTACAACGACACCGAAG (SEQ ID NO: 3) in the nucleotide sequence of orf79 are introduced into mitochondria, and/or a pair of TALENs, namely, TALEN binding to TTGCTAAAGTATCAGGC (SEQ ID NO: 4) in the nucleotide sequence of orf79 and TALEN binding to TTTTCCATTAAAGCCGG (SEQ ID NO: 5) in the nucleotide sequence of orf79 are introduced into mitochondria, so that one or more double-strand breaks can be introduced into orf79, to greatly change the mitochondrial genomic structure near orf79, and thereby to delete the orf79.

A third embodiment of the present invention relates to: a mitochondrial genome, in which a structural change has been induced by introducing a double-strand break into any given region of plant mitochondrial genomic DNA; mitochondria having the mitochondrial genome; a plant cell having the mitochondrial genome; a cytoplasm of the plant cell; and a seed and a plant (a mature plant body) comprising the plant cell.

A fourth embodiment of the present invention relates to: a mitochondrial genome, in which at least one gene has been deleted by introducing a double-strand break onto a gene that is present in a plant mitochondrial genome or DNA near the gene; mitochondria having the mitochondrial genome; a plant cell having the mitochondrial genome; a cytoplasm of the plant cell; and a seed and a plant (a mature plant body) comprising the plant cell.

The plant (mature plant body) according to the third and fourth embodiments of the present invention does not only include the generation of a mature plant body that has been differentiated from transformed cells obtained by introducing double-stranded DNA into mitochondrial genomic DNA (T0 generation), but it also includes a progeny generation obtained from the T0 generation. In addition, the seed according to the third and fourth embodiments of the present invention does not only include seeds obtained from the above-described T0 generation, but it also includes seeds obtained from a progeny generation.

The plant according to the first to fourth embodiments of the present invention is not particularly limited, and any plant may be used as long as it is a seed plant. If some plants must be listed herein, examples of the plant that can be used in the present invention include: gramineous plants such as rice, wheat, corn, barley, rye, and sorghum; and cruciferous plants, such as plants belonging to genus Alyssum, genus Arabidopsis (Arabidopsis thaliana, etc.), genus Armoracia (Armoracia rusticana, etc.), genus Aurinia, genus Brassica (Tatsoi, leaf mustard, Indian mustard, rapeseed, potherb mustard, Borec (Kale), ornamental cabbage, cauliflower, cabbage, brussels sprouts (Komochikanran), broccoli, bok choy, cole, rape, Chinese cabbage, Japanese mustard spinach, turnip, etc.), genus Camelina, genus Capsella, genus Cardamine, genus Coronopus, genus Diplotaxis, genus Draba, genus Eruca (rucola, etc.), genus Hesperis, genus Hirschfeldia, genus Iberis, genus Ionopsidium, genus Lepidium, genus Lobulari, genus Lunaria, genus Malcolmia, genus Matthiola, genus Nasturtium, genus Orychophragmus, genus Raphanus (Japanese white radish, radish, etc.), genus Rapistrum, genus Rorippa, genus Sisymbrium, genus Thlaspi, and genus Eutrema (wasabi, etc.). More examples of the plant that can be used herein include: solanaceous plants such as tomato, potato, green pepper, sweet pepper, and petunia; asteraceae plants such as sunflower and dandelion; Convolvulaceae plants such as morning glory and sweet potato; Araceae plants such as konjac, taro, dasheen, and hoopoe; leguminous plants such as soybean, red bean, and green bean; Cucurbitaceae plants such as pumpkin, cucumber, and melon; and Amaryllidaceae plants such as onion, spring onion, and garlic.

The disclosures of all publications cited in the present description are incorporated herein by reference in their entirety. In addition, when singular terms with the articles "a," "an," and "the" are used in the present description as a whole, these terms do not only include singular articles, but also include plural articles, unless otherwise clearly specified from the context.

Hereinafter, the present invention will be further described in the following examples. However, the examples are provided for illustrative purposes only, and are not intended to limit the scope of the invention.

EXAMPLES

1. Experimental Method 1-1. Construction of Plasmid

A mito-TALEN binary vector was constructed in accordance with the manual of Multisite Gateway Pro 3.0 Kit (Invitrogen), using Gateway (registered trademark) Technology. For the expression of TALENs that was to be transferred into mitochondria, a left TALEN monomer and a right TALEN monomer were each cloned into pDONR221 P1-P4 or pDONR221 P3-P2, and a mitochondrial localization signal derived from the ATPase δ' subunit of Arabidopsis thaliana (Sakamoto and Wintz, Plant Physiol. 112, 1736, 1996) was inserted into modified pH7WG2 (Karimi et al., Trends Plant Sci 7, 193-195, 2002) and modified pDONR P4r-P3r vectors, so that it could be expressed in the correct frame. Moreover, for termination of the left TALEN, a terminator derived from Arabidopsis thaliana HSP (At5g59720) (Nagaya et al., Plant Cell Physiol 51, 328-332, 2010) was inserted into pDONR P4r-P3r. Regarding a mito-TALEN 2 vector, a custom TALEN construct constructed in pDONR221 was acquired from Invitrogen. Regarding a mito-TALEN 3 vector, a custom TALEN construct was acquired from Cellectis Bioresearch (France), and then an EcoRV-XbaI fragment of the left TALEN and a BsaI-XbaI fragment of the right TALEN derived from the custom TALEN construct were cloned into modified pDONR221 vector.

1-2. Plant Materials

A rice strain BTA with cytoplasmic male sterility was produced by continuous back crossing in accordance with Shinjo et al. (Shinjo et al., Journal of Genetics 44, 149-156, 1969). The cytoplasm donor *Oryza sativa* L. subsp. Indica Chinsurah Boro II was subjected to continuous back crossing with the pollen parent japonica cultivar Taichung 65 (Kazama et al., Plant J 85, 707-716, 2016).

1-3. Genetically Recombinant Rice

Cultivation and transformation of plants were carried out according to the method described in Kazama et al., Plant J 85, 707-716, 2016. The T0 transformants were screened by PCR using a primer set for amplifying a hygromycin phosphotransferase portion (hpt). The T0 plants having such hpt were planted in a pot, and were then replanted in a greenhouse. The panicles of all of the T0 plants were covered with bags, in order to prevent cross-pollination, and thereafter, the number of T1 seeds was counted. Regarding the seed-setting degree, seeds were counted for at least three panicles (74 to 152 flowers appear from a single panicle) from each strain.

1-4. Preparation of Total DNA

Total DNA was extracted from the leaf blade, using DNeasy Plant Mini kit (Qiagen). A mitochondrial genomic structure near the target sequence of Mito TALEN was determined by PCR using the primers shown in table 2, and next-generation sequencing. Moreover, a Southern blot analysis was carried out base on the method described in Karimi et al., Trends Plant Sci 7, 193-195, 2002.

1-5. TAIL-PCR

A region outside of the deletion was amplified by (TAIL)-PCR (Singer et al., Methods Mol Biol 236, 241-272, 2003). In order to reduce pseudo-positive reactions, the FPNI-PCR-like (Wang et al., BMC Biotechnol 11, 109, 2011) arbitrary degenerate primers shown in Table 2 were used. The TAIL-PCR product was sequenced, and thereafter, the discovered connection site was confirmed by performing PCR, using novel primers established near the site. All of the primer pairs used in the TAIL-PCR analysis are shown in Table 2 and Table 3.

TABLE 2

| Primer name | Sequence (5' to 3') | Remarkes |
|---|---|---|
| tubulin_zF | TGGTCGGATTCGCCCGCTG (SEQ ID NO: 6) | for tubuline gene |
| tubulin_zR | TTACATGTCGTCAGCCTCCT (SEQ ID NO: 7) | for tubuline gene |
| HPT_zF | GAGAGCCTGACCTATTGCAT (SEQ ID NO: 8) | for hygromysine phosphotransferase |
| HPT_zR | TCGGCGAGTACTTCTACAOA (SEQ ID NO: 9) | for hygromysine phosphotransferase |
| BT_orf108_F1 | TCTTGGTCAAGAAGAAGGAC (SED ID NO: 10) | for a fragment x in FIG. 3 |
| BT_orf108_R1 | GCGGTGAATATGTGAACGG (SEQ ID NO: 11) | for a fragment x in FIG. 3 |
| BT_orf76_F1 | CTTATGCTAGCTTCGTACG (SEQ ID NO: 12) | for a fragment ix in FIG. 3 |
| BT_orf76_R1 | TTCAACCAGTTCTAGGGTTC (SEQ ID NO: 13) | for a fragment ix in FIG. 3 |
| BT_lack_F3 | TCTTCCATCAGGCCAAAACC (SEQ ID NO: 14) | for a fragment viii in FIG. 3 |
| BT_lack_R3 | AGAGGTGTTGATGCGGGATT (SEQ ID NO: 15) | for s fragment viii in FIG. 3 |
| BT_lack_F2 | GAGTGAGCTTCTGCACAGTA (SEQ ID NO: 16) | for a fragment vii in FIG. 3 |
| BT_lack_R2 | AGGACCCTTAGGCTTCACTT (SEQ ID NO: 17) | for a fragment vii in FIG. 3 |
| BT_orf82_F1 | GTAGTTCCGTCGGAAAGAA (SEQ ID NO: 18) | for a fragment vi in FIG. 3 |
| BT_orf82_R1 | ATCGGTCTAGAGCGAGTTTG (SEQ ID NO: 19) | for a fragment vi in FIG. 3 |
| BT_lack_F4 | GTGTAAAGGAATGGCTGCAG (SEQ ID ND: 20) | for a fragment v in FIG. 3 |
| BT_lack_R4 | TAGGTAGGTAGGCTTCACTG (SEQ ID NO: 21) | for a fragment v in FIG. 3 |
| BT_lack_F5 | CCAAAGTCACTCTTCCACTG (SEQ ID NO: 22) | for a fragment iv in FIG. 3 |
| BT_lack_R5 | TACTTGATCAGACTTCGCCC (SEQ ID NO: 23) | for a fragment iv in FIG. 3 |
| R12F_no5_F1 | TCCTCGTGGAGGATTTCTGTTCA (SEQ ID NO: 24) | for a fragment iii in FIG. 3 |
| R12F_no5_R1 | GGCASTATTGGACTCCGTTCTCAT (SEQ ID NO: 25) | for a fragment iii in FIG. 3 |
| BT_lack_F6 | GGTCCTCCTAGAGATAGGATA (SEQ ID NO: 26) | for a fragment ii in FIG. 3 |
| BT_lack_R6 | AACCTGAAGAGCAGTACCTC (SEQ ID NO: 27) | for a fragment ii in FIG. 3 |
| ORF79-F1 | ACCAACGCCGACCCCCAAACAA (SEQ ID NO: 28) | for a fragment i in FIG. 3 |
| ORF79-R1 | CTTAGGAAAGACTACACGAATAGAGGTGCCCC (SEQ ID NO: 29) | for a fragment i in FIG. 3 |
| atp6-Fk | ATAGGCATTACGACTCGTTGG (SEQ ID NO: 30) | for a FPNI-PCR-like arbitrary degenerate primer (in 1st TAIL-PCR) |
| atp6-Rk | GGACCAAGATCTCCTATGAA (SEQ ID NO: 31) | for a fragment i in Extended Data T1 progeny PCR |
| cox2-Fk | CAGTTCGATGAACAGTCAC (SEQ ID NO: 32) | for a FPNI-PCR-like arbitrary degenerate primer (in 1st TAIL-PCR) |
| cox2-Rk | TCTCGTTGTACCGAGATGGA (SEQ ID NO: 33) | for a control in Extended Data T1 progeny PCR |
| FP-AD1 | GTAATACGAC7CACTATAGGGCACGCGTCGTNGTCGASWGAN AWGAA (SEQ ID NO: 34) | for a FPNI-PCR-like arbitrary degenerate primer (in 1st TAIL-PCR) |
| FP-AD2 | GTAATACCACTCACTATAGGCCACGCGTGGTTGWGNAGSANC ASAGA (SEQ ID NO: 35) | for a FPNI-PCR-like arbitrary degenerate primer (in 1st TAIL-PCR) |
| FP-AD3 | GTAATACGACTCACTATAGGGCACGCGTGGTAGWGNAGWANC AWACG (SEQ ID NO: 36) | for a FPNI-PCR-like arbitrary degenerate primer (in 1st TAIL-PCR) |
| FP-AD6 | GTAATACGACTCACTATAGGSCACGCGTGGTWGTGNAGWANC ANAGA (SEQ ID NO: 37) | for a FPNI-PCR-like arbitrary degenerate primer (in 1st TAIL-PCR) |
| FP-FP6 | GTAATACGACTCACTATAGGCCACGCGTGGTNGACGASWGAN AWGAC (SEQ ID NO: 38) | for a FPNI-PCR-like arbitrary degenerate primer (in 1st TAIL-PCR) |
| FP-FP9 | GTAATACGACTCACTATAGGCCACGCGTGGTNCAGCTWSCTNT SCTT (SEQ ID NO: 39) | for a FPNI-PCR-like arbitrary degenerate primer (in 1st TAIL-PCR) |
| no. 9-F1 | TGTCGCATTCCTACCACTGCTT (SEQ ID NO: 40) | for a gene specific pruner (in 1st TAIL-PCR) |
| no. 10-F3 | CATTGGTTASTTAAGTAATTGCATTTCCGCTTC (SEQ ID NO: 41) | for a gene specific primer (in 1st TAIL-PCR) |
| no. 11-F3 | CCTAACTAGGAGACAGGTCTGATAAAAAGAG (SEQ ID NO: 42) | for a gene specific primer (in 1st TAIL-PCR) |
| no. 12-F3 | ATGCCCTTAGAGAAAGAAGTGAGCCT (SEQ ID NO: 43) | for a gene specific primer (in 1st TAIL-PGR) |
| no. 14-F3 | GATATTTCGTTGGTCACCAGAATTCCATAG (SEQ ID NO: 44) | for a gene specific primer (in 1st TAIL-PCR) |
| ATP6-F3 | GCGTTCCTTGGACTATGCTATTTCTGAATAA (SEQ ID NO: 45) | for a gene specific primer (in 1st TAIL-PCR) |
| FSP1 | GTAATACGACTCACTATAGGGC (SEQ ID NO: 46) | for a FPNI-PCR-like FSP1 primer (in 2nd TAIL-PCR) |

TABLE 2 -continued

| Primer name | Sequence (5' to 3') | Remarkes |
|---|---|---|
| no. 9-F2 | AGCAAGCGCTATTAAAGGGCGCAG (SEQ ID NO: 47) | for a gene specific primer (in 2nd TAIL-PCR) |
| no. 10-F2 | TAGAGAATCTAGTACAGCTATCTACGAGACGAGAA (SEQ ID NO: 48) | for a gene specific primer (in 2nd TAIL-PCR) |
| no. 11-F2 | CTACTCACTCGATTTCGAAGAGCTGC (SEQ ID NO: 49) | for a gene specific primer (in 2nd TAIL-PCR) |
| no. 12-F2 | GTATGGGAGTTGAATCATAAGTAACTCCTAGACC (SEQ ID NO: 50) | for a gene specific primer (in 2nd TAIL-PCR) |
| no. 14-F2 | AGCTCGTAATGAATTGATTCGAACCAATATCTC (SEQ ID NO: 51) | for a gene specific primer (in 2nd TAIL-PCR) |
| ATP6-F4 | ACCGGTTCGGAATTAGGTGTAGCTATATTACAAG (SEQ ID NO: 52) | for a gene specific primer (in 2nd TAIL-PCR) |
| no. 16-F1 | CAACGATTAGAGAGAGTAGGGAGTACCGTTCAT (SEQ ID NO: 53) | for a gene specific primer (in 2nd TAIL-PCR) |
| n10s-99t-F1 | CATCATAGGTCTTGCAGCGTCTTGAG (SEQ ID NO: 54) | for the confirmation of TAIL-PCR amplification |
| n10s-99t-R1 | AGGGTTCGTATTCGGGTCACAACA (SEQ ID NO: 55) | for the confirmation of TAIL-PCR amplification |
| no. 13-F1 | GTGAGCCATGCCATAACTTGCCCA (SEQ ID NO: 56) | for the confirmation of TAIL-PCR amplification |
| R12F_no4_F1 | AGCAGGCTTCAGCCGTATCTT (SEQ ID NO: 57) | for the confirmation of TAIL-PCR amplification |
| R12F_no5_F1 | TCCTCSTGGAGGGATTTCTGTTCA (SEQ ID NO: 58) | for the confirmation of TAIL-PCR amplification |
| R12F_no6_F1 | AGCTGCCCTTGCTTTTCCTTCA (SEQ ID NO: 59) | for the confirmation of TAIL-PCR amplification |
| orf79-k1-Fw | CTTGAATGATGCTATAAATCTOC (SEQ ID NO: 60) | for the confirmation of TAIL-PCR amplification |
| sg1-62-F1 | ACTACAGAAATGTAGCGAGCCG (SEQ ID NO: 61) | for the confirmation of TAIL-PCR amplifination |
| TAL2-4-R1 | TCTTTCCTCGGCTTCCTACACGG (SEQ ID NO: 62) | for the confirmation of TAIL-PCR amplification |
| TAL2-5-R1 | CTTGCTTCCCATTGTCATTCCCATTGT (SEQ ID NO: 63) | for the confirmation of TAIL-PCR amplification |
| TAL3-6-F2 | ACTGGTCTAGTTAACCCAGAGGAGGAATATAC (SEQ ID NO: 64) | for the confirmation of TAIL-PCR amplification |
| TAL3-6-R1 | GAAGGAACAAATCCTCGTATTGAAACCGGTC (SEQ ID NO: 65) | for the confirmation of TAIL-PCR amplification |
| TAL3-9-R1 | GACCGGTGTGTGATTCAGCTCC (SEQ ID NO: 66) | for the confirmation of TAIL-PCR amplification |
| atp6_F1 | AGGGTATGATACCCTTTAGC (SEQ ID NO: 67) | for atp6 probe |
| atp6_R1 | GAGATCGTAGAAACATGAGC (SEQ ID NO: 88) | for atp6 probe |
| 8-GSP6 | ATGGCAAATCTGGTCCGATG (SEQ ID NO: 69) | for orf79 probe |
| 8-GSP1 | AGGGGTGGGATATTGCCTGGTCCACC (SEQ ID NO: 70) | for orf79 probe |
| nr1 5'_F2 | CAAATAGGAAAGTGGAGGGT (SEQ ID NO: 71) | for the probe1 in FIG. 4 |
| nr1 5'_R2 | CGTATGACGTCTCAGTCTGT (SEQ ID NO: 72) | for the probe1 in FIG. 4 |
| nr1_3'_F2 | GCCTGAACCTATAGGTTCGT (SEQ ID NO: 73) | for the probe2 in FIG. 4 |
| nr1_3'_R2 | TTACGCCCTAAATGCTGAAC (SEQ ID NO: 74) | for the probe2 in FIG. 4 |

TABLE 3

| | | | 1st TAIL-PCR | | | | | | 2nd TAIL-PCR | | Primer set for |
| | | | AD (arbitrary degenerate) primers | | | | | | | | |
| Lines | | Gene-specific primer | FP-AD1 | FP-AD2 | FP-AD3 | FP-AD6 | FP-FP6 | FP-FP9 | Gene-specific primer | FSP1 primer | the confirmation of TAIL-PCR amplification |
|---|---|---|---|---|---|---|---|---|---|---|---|
| #2-2 | hr7 | no. 10-F3 | | | | | ✓ | | no. 10-F2 | FSP1 | no. 10-F1/no10s-99t-R1 |
| #2-3 | hr8 | no. 10-F3 | | ✓ | | | ✓ | | no. 10-F2 | | R12F_no5-F1/TAL2-4-R1 |
| #2-4 | hr5 | no. 9-F1 | | ✓ | ✓ | ✓ | | | no. 9-F2 | | R12F_no5-F1/TAL2-4-R1 |
| #2-5 | hr2 | no. 12-F3 | | ✓ | ✓ | | | | no. 12-F2 | | no. 13-F1/TAL2-5-R1 |
| #2-7 | hr7 | no. 10-F3 | | ✓ | ✓ | | | ✓ | no.10-F2 | | no. 10-F1/no10s-99t-R1 |
| #3-1 | hr9 | no. 10-F3 | | ✓ | | | | | no. 10-F2 | | R12F_no6-F1/TAL3-6-F2 |
| #3-3 | hr5 | no. 9-F1 | ✓ | | | | | | no. 9-F2 | | R12F_no5-F1/TAL2-4-R1 |
| #3-6 | hr6 | no. 9-F1 | ✓ | | | | | | no. 9-F2 | | R12F_no5-F1/TAL3-6-R1 |
| #3-9 | hr4 | no. 11-F3 | ✓ | | | | | | no. 11-F2 | | R12F_no4-F1/TAL3-9-R1 |
| #3-10 | hr7 | no. 10-F3 | | | | | ✓ | ✓ | no. 10-F2 | | no. 10-F1/no10s-99t-R1 |
| #3-11 | hr10 | no. 14-F3 | ✓ | | | ✓ | | ✓ | no. 14-F2 | | no. 10-F1/sg1-62-F1 |
| #3-11 | hr11 | ATP6-F3 | | ✓ | | | | | ATP6-F4 | | orf79-k1-Fw/no10s-99t-F1 |

(✓: tested and amplified)

1-6. Genome Sequence and Assembly

Total DNA was extracted from the leaf blades of an untransformed BTA plant, 8 strains (#2-1, #2-4, #3-1, #3-2, #3-3, #3-9, #3-10, and #3-11) of T1 plants, and 2 strains of T0 plants that could not have seeds. Before DNA was extracted from the T1 plants, the presence or absence of an introduced gene was confirmed by PCR using the HPT primer set (Table 2). Preparation of a library and sequencing (Illumina HiSeq 4,000) were carried out by Macrogen Inc. (Japan). A 350-bp paired end libraries having different tags were used to perform sequencing in a single lane. All reads were within a range from 4.1 to 6.7 Gb. A total of 40-66 Mb from each library was mapped on a reference sequence of a BTA mitochondrial genome (536 kb) (Accession Nos.: AP017385 (Subgenome 1) and AP017386 (Subgenome 2)), using BWA-MEM.

2. Results

2-1. Knocking Out of Mitochondrial Orf79 Using Mito TALENs

Figure 1C:
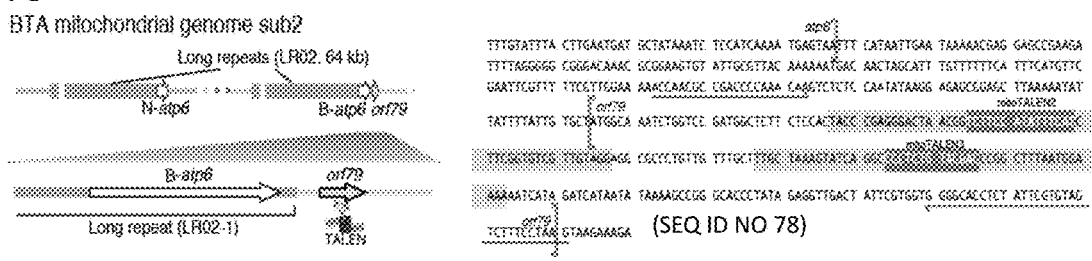

In order to transfer TALENs into mitochondria, a mitochondrial-localizing sequence (MLS) was ligated to the N-terminus (FIG. 1A). Such TALENs that target mitochondria (which are referred to as "mito-TALENs") have been used also in mammalian cells (Bacman et al., Nat Medicine 19, 1111-1113, 2013; Reddy et al., Cell 161,459-469, 2015). However, such mito-TALENs have not been used so far in more complicated plant mitochondria. In order to allow the mito-TALENs to express in plants, we have constructed an entry vector and a destination vector, which were to be used in Gateway (registered trademark) cloning, and thereafter, we have produced an *Agrobacterium*-mediated transformation vector (two types of mito-TALEN expression vectors targeting different sites of orf79; FIG. 1i), to the N-terminus of which MLS (a mitochondrial localization signal peptide) was added, and which expressed two different proteins simultaneously (FIG. 1A). The two vectors mito-TALEN2 (#2) and mito-TALEN (#3) (FIG. 1C) were each introduced into the callus of CMS (orf79+) rice strain BTA, separately, and thereby, the transformants 7 (#2-1 to #2-7) and 11 (#3-1 to #3-11) were obtained.

Figure 2A:
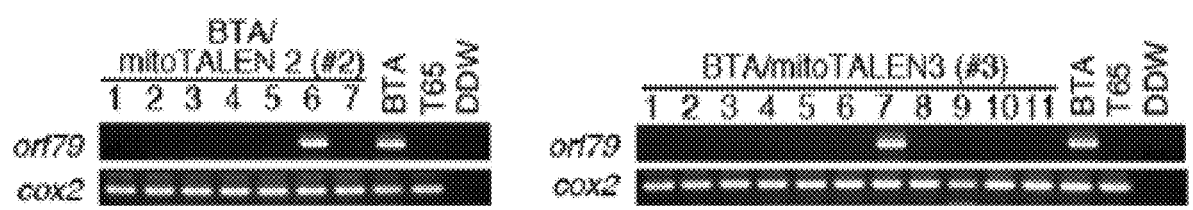
FIGS. 2A and 2B show confirmations of the knockout of orf79.
Figure 2B:
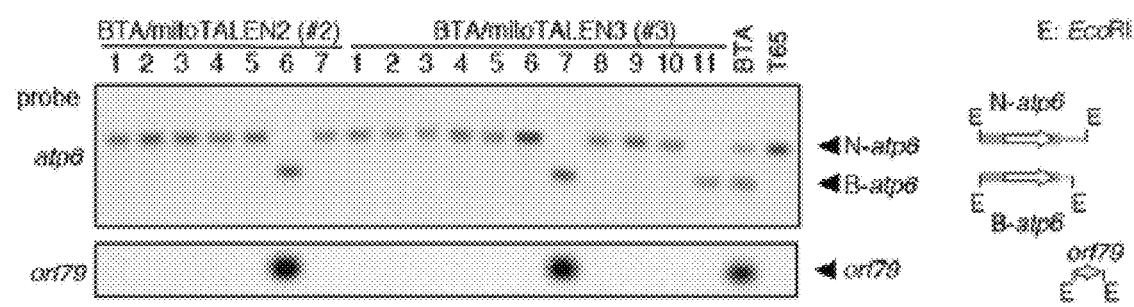

It was confirmed by PCR that, after completion of the transformation, orf79 was knocked out in all transformants except for two transformants (FIG. 2A). Moreover, it was also confirmed by Southern blotting that orf79 was knocked out in the transformants (the lower blot in FIG. 2B). When the mitochondrial genome of plants is studied, it is considered to be circular DNA called "master circle" comprising all genetic information. However, in the case of the sterile rice strain BTA, which differs from other cultivars, the mitochondrial genome is considered to be two circular DNAs, which are referred to as "Subgenome 1" and "Subgenome 2." orf79 is present downstream of the B-atp6 gene of Subgenome 2, and it is positioned at the end of LR02-1 (64 kb) as a long repeated structure (LR) (see left view of FIG. 1C). The upper blot of FIG. 2B shows that the band corresponding to B-atp6 disappeared in almost all transformants. From these results, it became clear that not only a deletion of the target gene, but also a deletion of other genomic regions is induced by introduction of a double-stranded break into mitochondrial genomic DNA with the use of TALENs.

2-1. Deletion Near Orf79, and Recombination Mediated by Homologous Sequence

Figure 3A:
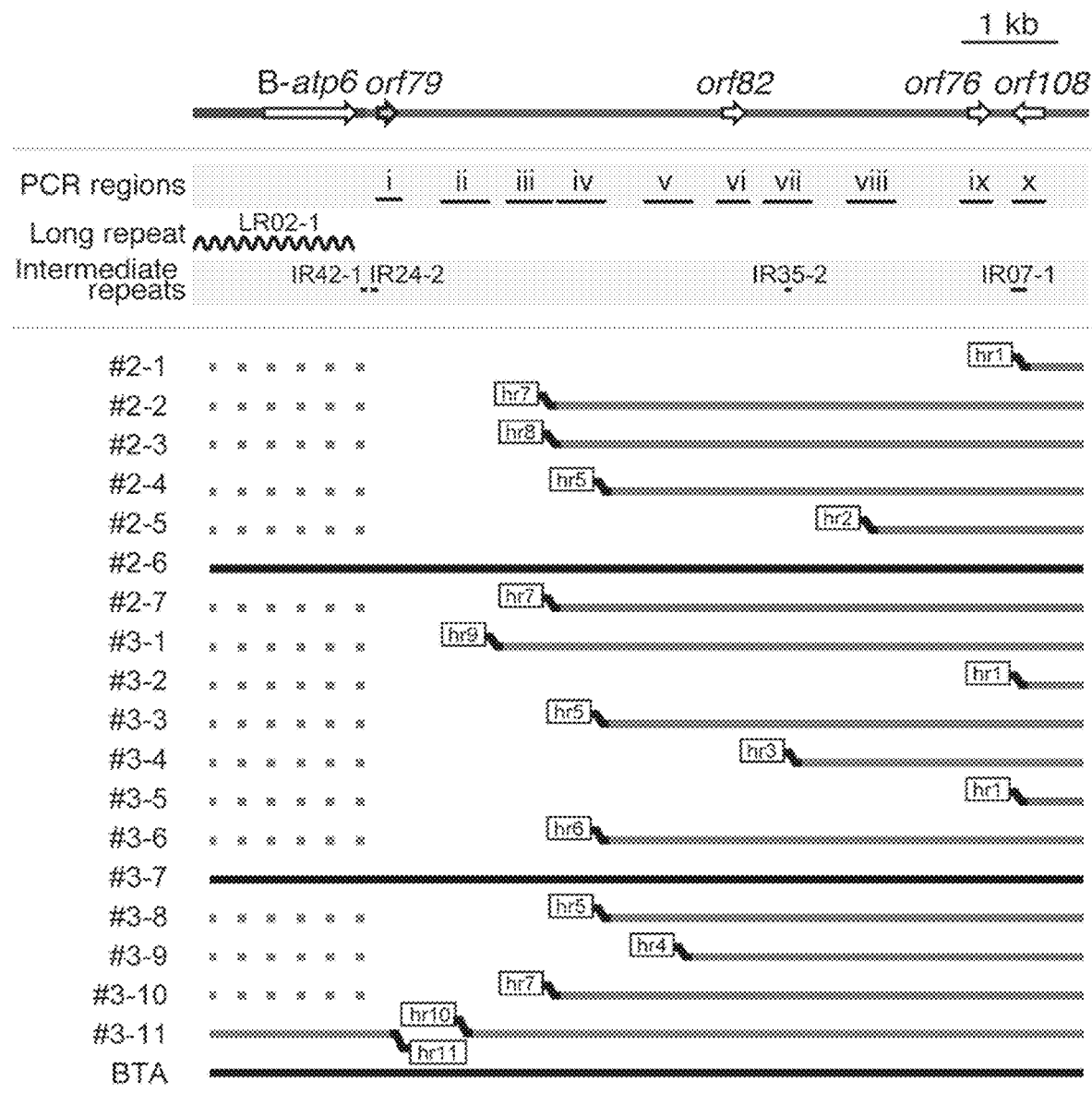
FIGS. 3A and 3B show deletion and homologous recombination near orf79 (1).
Figure 3B:
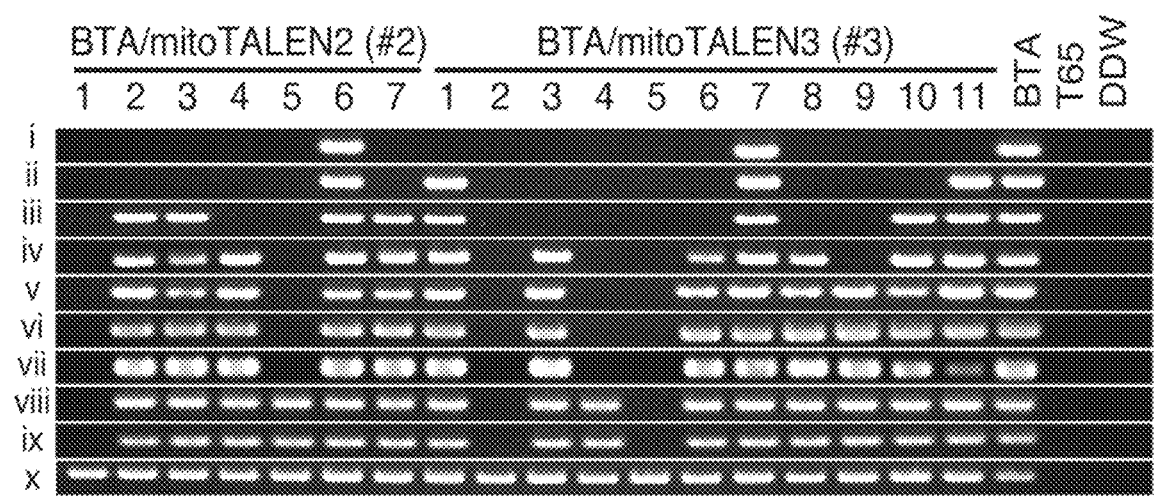

In order to determine a deleted region around orf79, whether or not 10 regions between orf79 and orf108 (see upper view of FIG. 3A) were present in transformants was analyzed by PCR. As a result, all transformants had orf108, but some transformants lacked a region present in the middle between orf79 and orf108. Such a deleted region included orf76 and/or orf82. It was found that #2-1, #3-2 and #3-5 had the longest deletion in this region (FIGS. 3A and 3B). On the other hand, #3-11 had the shortest deletion, and had only a deletion of a region around orf79 (FIGS. 3A and 3B). In order to examine whether or not the DNA terminus was directly rejoined by the double-strand break of the DNA, an attempt was made to amplify by PCR a region that was considered to be rejoined. However, no amplification products were obtained. These results demonstrate that even if a double-strand break is introduced into plant mitochondrial genomic DNA, repair by nonhomologous end-joining (NHEJ) does not take place.

Figure 4A:
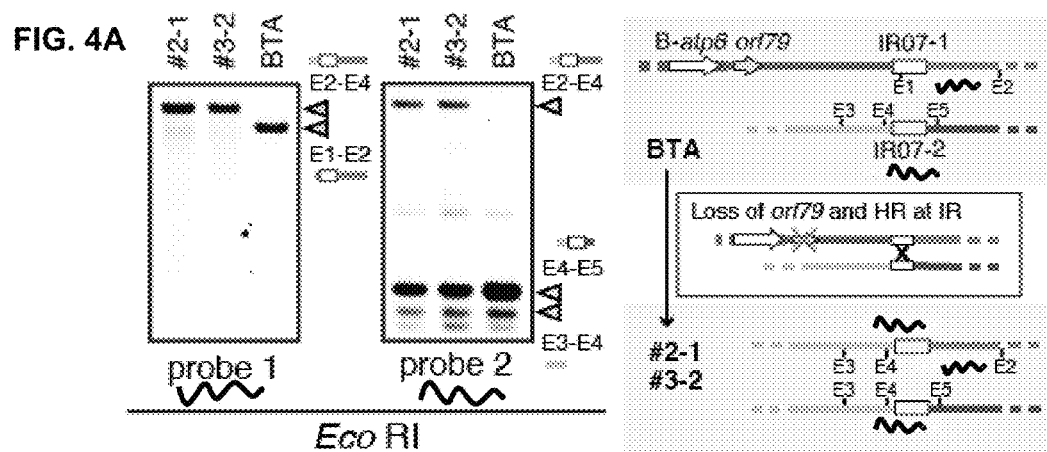
FIGS. 4A and 4B show deletion and homologous recombination (2) near orf79.

As a phenomenon that may occur after the introduction of a double-strand break, other than the nonhomologous end-joining, it has been predicted that the open end would be recombined with a homologous DNA sequence, and that it would be connected with a different position on the mitochondrial genome. The plant mitochondrial genome comprises many homologous sequences including long repeated sequences reciprocally rebinding with one another at a high frequency (LRs; >501 bp) and middle-sized repeated sequences rebinding with one another sporadically and nonreciprocally (IRs; 51 to 500 bp). As a result of searching for repeated sequences near orf79, it was found that a 64-kb repeated sequence (LR02-1) comprising B-atp6, and IR07-1 and IR35-2 were present (FIG. 3A). Moreover, it was also found that another IR07 copy (IR07-2) was present at a site 82 kb downstream of IR07-1 (FIG. 4A). From the results of Southern blotting (FIG. 4A), it was demonstrated that nonreciprocal homologous recombination was generated between two IR07-1 in #2-1, and that it formed a novel DNA connection. The same phenomenon occurred also in #3-2 and #3-5. Nonreciprocal homologous recombination in other two IR35s was found at the end of the deleted portion of #3-4 (FIGS. 3A and 3B).

Figure 4B:
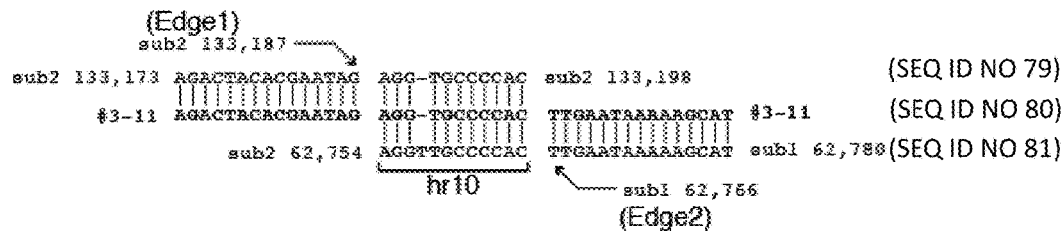

The IRs, which had been re-bound after the introduction of a double-strand break into DNA near orf79, was not found in any other strains (FIG. 3A). Hence, an attempt was made to determine a sequence near the deleted region by TAIL-PCR. Interestingly, in #3-11, the neighboring sequence was connected with the same sequence of Subgenome 1, and the connection site between these sequences had a common 11-bp sequence (FIG. 4B). These results demonstrate that one of the open ends is connected with a different position via a pair of short homologous sequences according to homologous recombination. It was confirmed that all open ends derived from other transformants are also ligated to a site apart therefrom having a short common sequence (11 to 47 bp). These results were also confirmed by the sequencing of a PCR amplicon amplified using novel primers (FIG. 5).

Figure 6A:
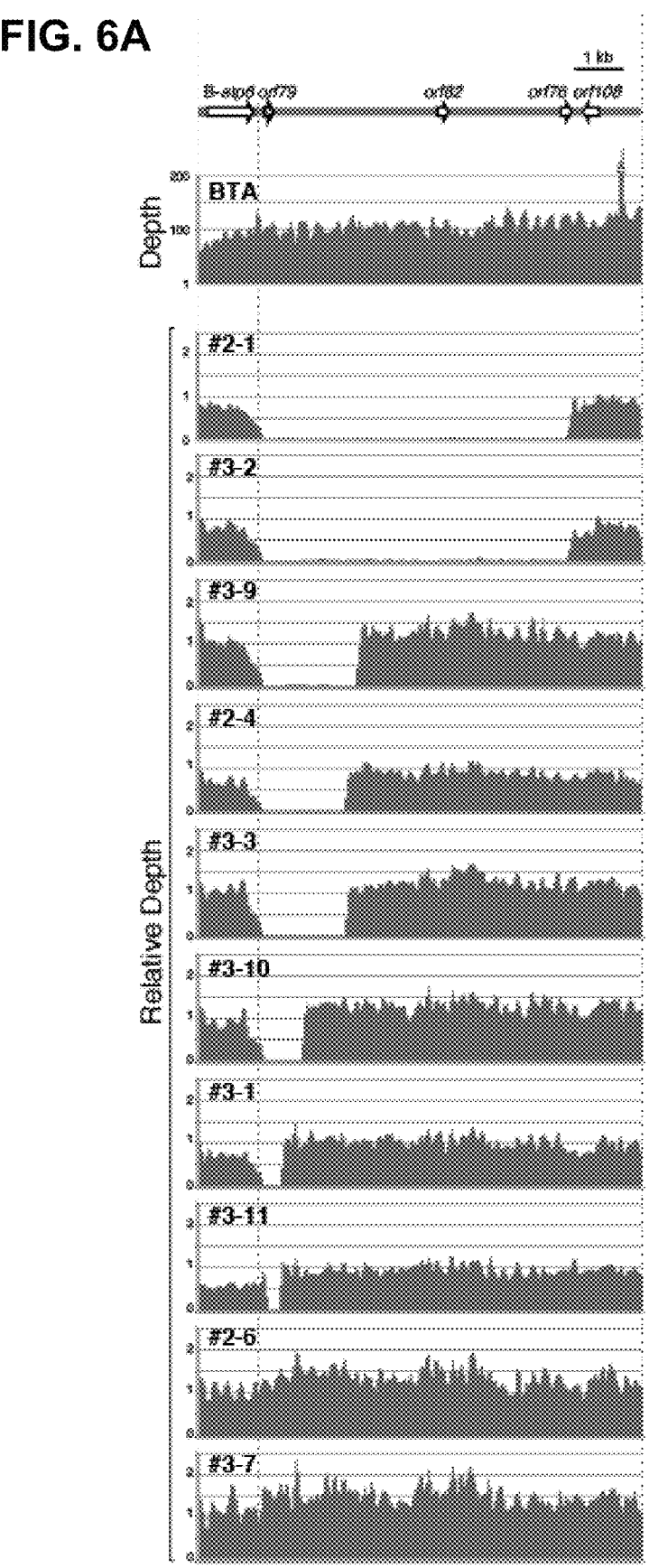
FIGS. 6A and 6B show the influence of a deletion of mitochondrial DNA on BTA and transformants.
Figure 6B:
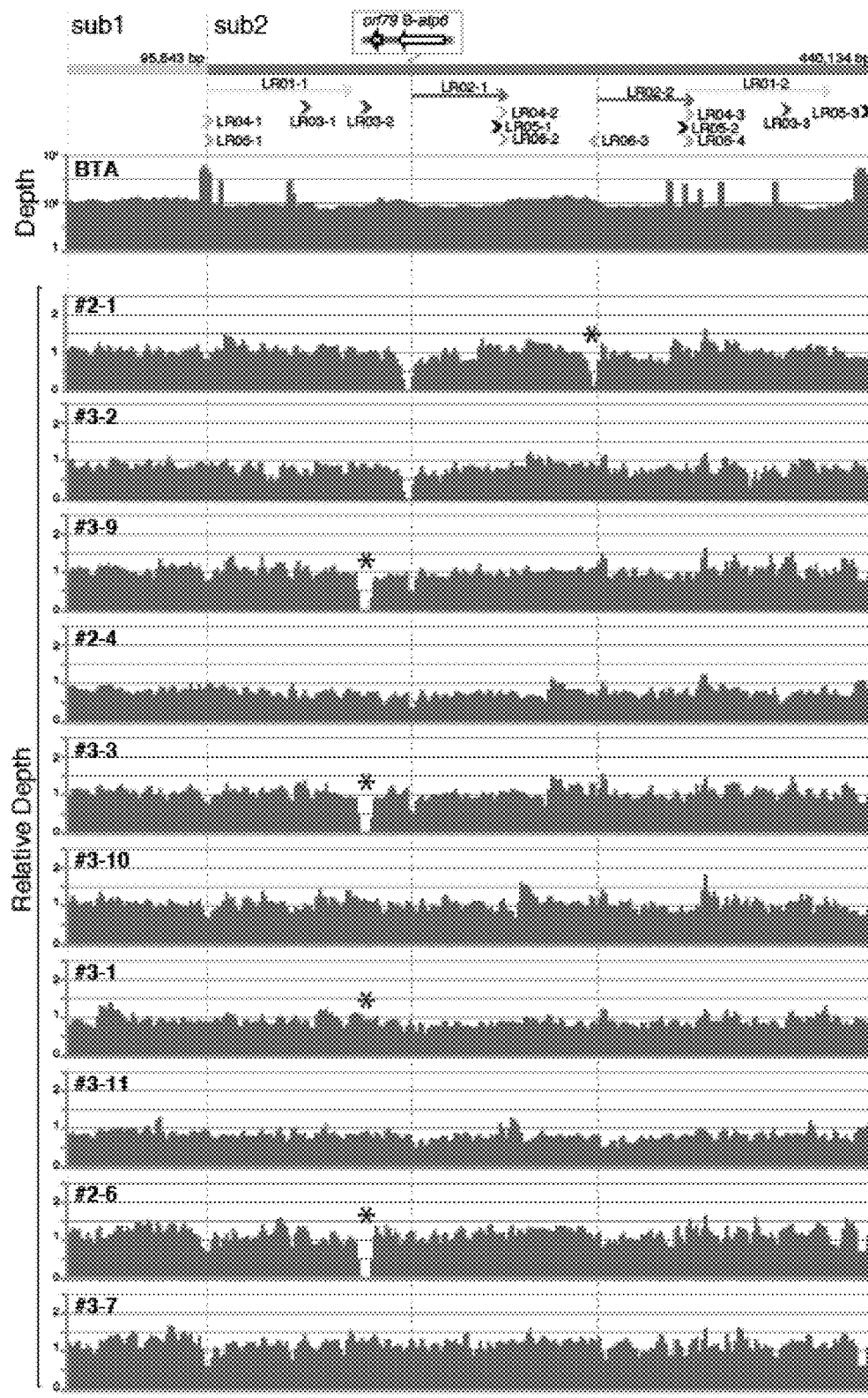

2-3. Influence of Mitochondrial DNA Deletion of BTA and 10 Transformants by TALENs In order to examine the influence of the introduction of a double-strand break into DNA by mito-TALEN, the whole genome sequences of 10 transformants and untransformed BTA were sequenced. The reads of the nucleotide sequences were mapped on the mitochondrial genome of BTA serving as a reference sequence (FIGS. 6A and 6B). From the read depth of the sequence, a deletion near orf79 (a region in which the relative depth is 0 in FIGS. 6A and 6B) and individual homologous re-bound sequences shown in FIG. 3A (hr1 to hr11) could be confirmed. In addition, from the data of read depth, it could be confirmed that the copy number was not influenced by editing with mito-TALEN in almost all mitochondrial genomic regions other than the deleted region. Moreover, it was confirmed that several ORFs with unknown functions were not present, but that all genes, the functions of which had been assumed, were present in the mitochondrial genome of all transformants. From the aforementioned results, it was found that various deletions occurred in the mitochondrial genome of each transformant, but that 1) an essential gene was not deleted in all of the transformants, 2) only the orf79 was a commonly deleted orf in the orf79-deficient strain, and 3) the copy number in other regions was maintained in almost all regions.

2-4. Reversion of Fertility

Figure 7A:
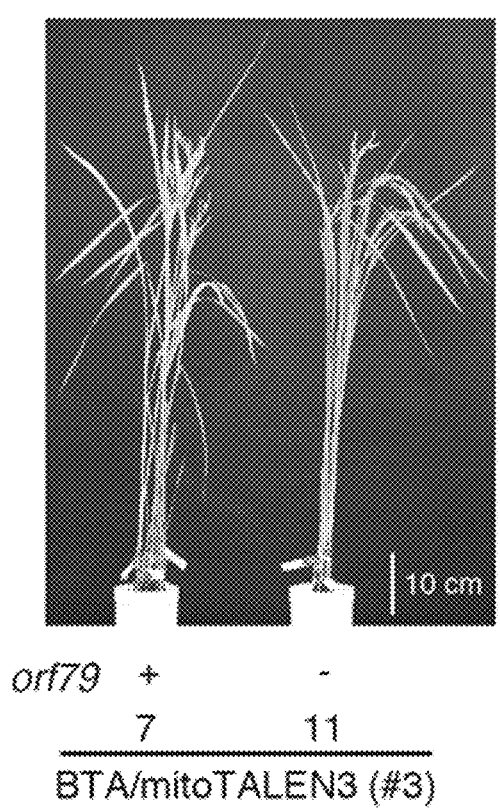
FIGS. 7A and 7B show studies regarding the reversion of fertility in orf79-lost BTA-CMS rice.
Figure 7B:
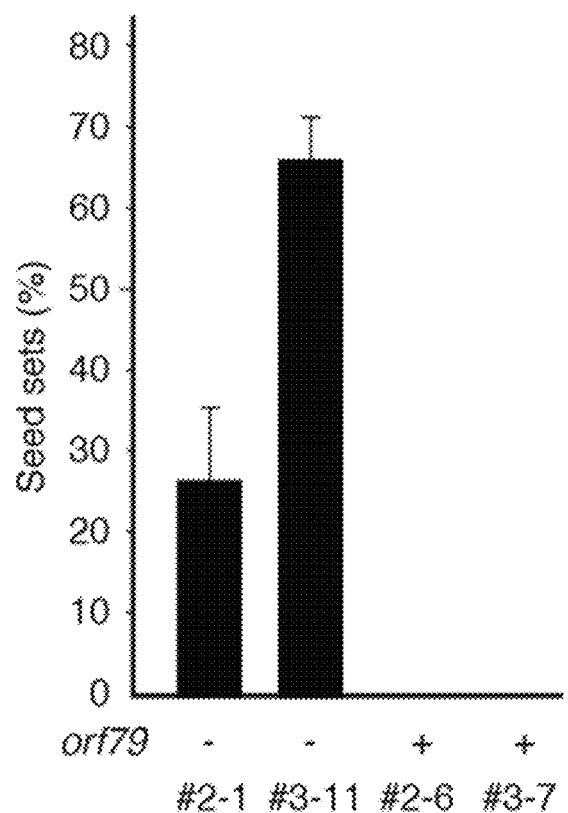
Figure 8A:
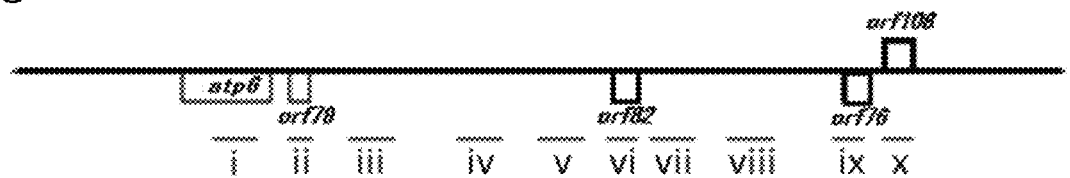
FIGS. 8A and 8B show the PCR analysis of the T1 generation of transformants. The results obtained by performing genotyping on mitochondrial genome and nucleus introduced genes in the T1 generation of the strain #3-10. The upper view schematically shows a gene structure around orf79. Amplification fragments used to confirm deletion are shown in i to x. The lower view shows the results obtained by performing genotyping on the mitochondria of the T1 generation obtained by self-pollination of the strain #3-10. As a positive control in a PCR reaction, a cox2 fragment was amplified. Since the amplification fragments ii to x were specifically present in BTA, they were not amplified in T65. It was confirmed that HPT and Fok I present in a mito-TALEN expression cassette were present. The strain 5 of the T1 generation lost a mito-TALEN expression cassette.
Figure 8B:
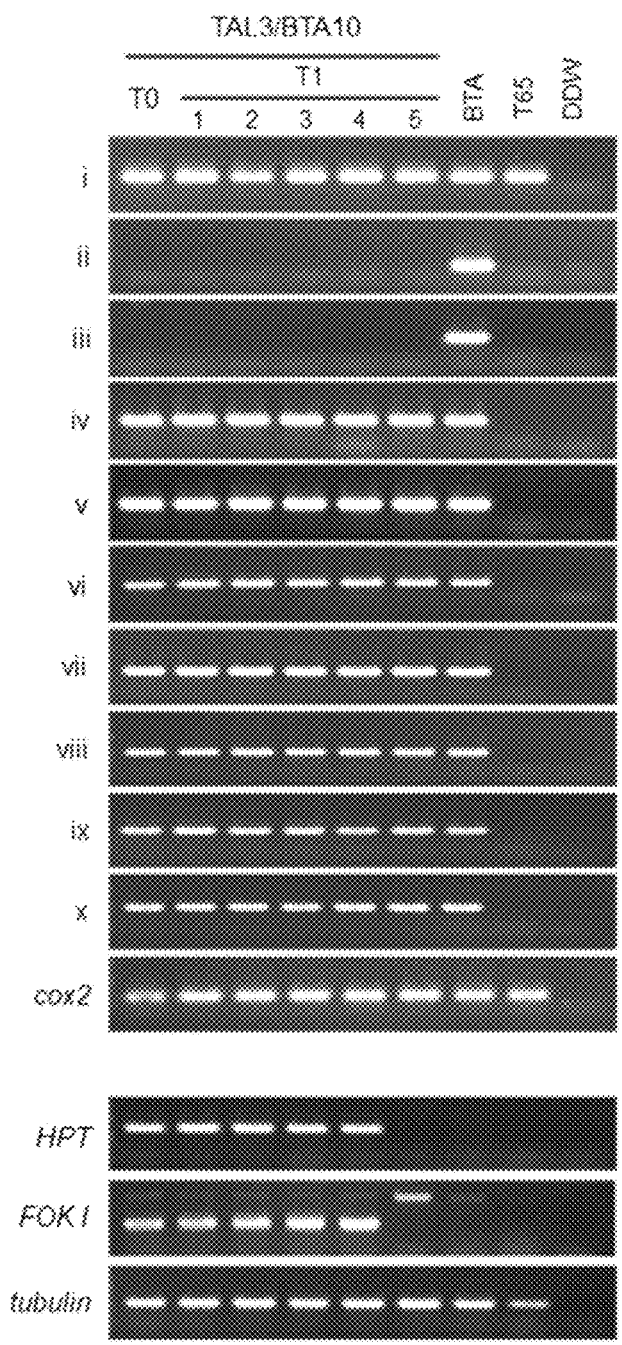

In order to confirm the reversion of fertility in transformants, panicles were covered with bags to prevent crossbreeding, and thereafter, the number of T1 seeds was counted. T1 seeds were obtained from orf79-deleted transformants (#2-1 and #3-1), but transformants having orf79 (#2-6 and #3-7) were still sterile, as with the original BTA (FIG. 7B). In all of the transformants, other abnormal phenotypes were not found (FIG. 7A). Several T1 progenies that had been obtained by self-pollination were subjected to a PCR analysis. As a result, it was found that the deletion in each transformant was maintained, at least, until the next generation (FIGS. 8A and 8B). From these results, it was suggested that the arrangement of the changed mitochondrial genome be stably inherited to the next generation, regardless of the inheritance of a mito-TALEN expression cassette (which was present in the nucleus).

From the above-described experimental results, it became clear that, when a double-strand break is introduced into the mitochondrial genomic DNA of a plant, a large deletion occurs around the cleavage site, repair takes place due to recombination mediated by a homologous sequence near the cleavage site, and as a result, a structural change is induced to the mitochondrial genome.

INDUSTRIAL APPLICABILITY

By applying the method according to the present invention, a structural change can be induced in a plant mitochondrial genome. Therefore, the method of the present invention enables not only a deletion of a desired mitochondrial gene, but also the creation of novel orf, mediated by a structural change in the mitochondrial genome.

What is claimed is:

1. A method for inducing a deletion of a portion of a mitochondrial genome and/or rearrangement resulting in a novel mitochondrial genomic DNA sequence in a plant cell, comprising:

introducing a double-strand break into a target sequence region present in multiple individual mitochondrial genomic DNA molecule species in the plant cell in a target sequence specific manner by introducing a TALEN directed at said target sequence region fused with a plant-derived mitochondrial localization signal peptide into the cytoplasm of the plant cell, wherein the TALEN is introduced into mitochondria by cleavage of the plant-derived mitochondrial localization signal peptide.

2. The method according to claim 1, wherein the deletion of a portion of the mitochondrial genome and/or rearrangement resulting in a novel mitochondrial genomic DNA sequence is induced by DNA recombination occurring between a sequence that is present near the target sequence region and a homologous sequence thereof that is present in another region, after the double-strand break is introduced into the target sequence region.

3. A method for deleting a gene that is present in multiple individual mitochondrial genomic DNA molecule species in a plant cell, comprising:

introducing a double-strand break into the gene or a region near the gene in a target sequence specific manner by introducing a TALEN directed at said gene or said region near the gene fused with a plant-derived mitochondrial localization signal peptide into the cytoplasm of the plant cell, wherein the TALEN is introduced into mitochondria by cleavage of the plant-derived mitochondrial localization signal peptide.

4. The method according to claim 3, wherein the deletion of the gene is induced by DNA recombination occurring between the gene or a sequence that is present in a region near the gene and a homologous sequence that is present in another region, after the double-strand break is introduced into the gene or the region near the gene.

5. The method according to claim 3, wherein the gene is a gene responsible for male sterility.

6. The method according to claim 1, wherein an expression construct of the TALEN is prepared by a method comprising the following steps (a) to (c):

(a) a step of providing an entry vector 1, in which a TALEN left is inserted between two homologous recombination sequences L1 and L4, an entry vector 2, in which a terminator, a promoter and a plant-derived mitochondrial localization signal are inserted in this order between two homologous recombination sequences R4 and R3, and an entry vector 3, in which a TALEN right is inserted between two homologous recombination sequences L3 and L2;

(b) a step of providing a destination vector, into which a promoter, a plant-derived mitochondrial localization signal, a homologous recombination sequence R1 and a homologous recombination sequence R2 are inserted in this order; and (c) a step of mixing the entry vector 1, the entry vector 2, the entry vector 3 and the destination vector with one another, so that homologous recombination is allowed to take place between L1 and R1, between L4 and R4, between L3 and R3, and between L2 and R2.

7. The method according to claim 2, wherein the rearrangement resulting in a novel mitochondrial genomic DNA is induced by a novel DNA connection formed by homologous recombination.

* * * * *

SEQUENCE LISTING

```
<160> NUMBER OF SEQ ID NOS: 81

<210> SEQ ID NO 1
<211> LENGTH: 240
<212> TYPE: DNA
<213> ORGANISM: Oryza sativa

<400> SEQUENCE: 1
atggcaaatc tggtccgatg gctcttctcc actacccgag ggactaacgg tcttccatat      60
ttcatcttcg gtgtcgttgt aggaggcgcc ctgttgtttg ctttgctaaa gtatcaggcc     120
cctctgtacg acccggcttt aatggaaaaa atcatagatc ataatataaa agccgggcac     180
cctatagagg ttgactattc gtggtggggc acctctattc gtgtagtctt tcctaagtaa     240

<210> SEQ ID NO 2
<211> LENGTH: 19
<212> TYPE: DNA
<213> ORGANISM: Oryza sativa
```

```
<400> SEQUENCE: 2
tacccgaggg actaacggt                                                19

<210> SEQ ID NO 3
<211> LENGTH: 19
<212> TYPE: DNA
<213> ORGANISM: Oryza sativa

<400> SEQUENCE: 3
tcctacaacg acaccgaag                                                19

<210> SEQ ID NO 4
<211> LENGTH: 17
<212> TYPE: DNA
<213> ORGANISM: Oryza sativa

<400> SEQUENCE: 4
ttgctaaagt atcaggc                                                  17

<210> SEQ ID NO 5
<211> LENGTH: 17
<212> TYPE: DNA
<213> ORGANISM: Oryza sativa

<400> SEQUENCE: 5
ttttccatta aagccgg                                                  17

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
tggtcggatt cgccccgctg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
ttacatgtcg tcagcctcct                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
gagagcctga cctattgcat                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 9
tcggcgagta cttctacaca                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
tcttggtcaa gaagaaggac                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
gcggtgaata atgtgaacgg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
cttatgcgta ggttcgtacg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ttcaaccagt tctagggttc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tcttggatca ggccaaaacc                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
agaggtgttg atgcgggatt                                              20

<210> SEQ ID NO 16
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 16
gagtgagctt ctgcacagta                                           20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17 aggacccctta ggcttcactt                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
gtagttccgt cgggaaagaa                                           20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
atcggtctag agcgagtttg                                           20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
gtgtaaagga atgggtgcag                                           20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
taggtaggta ggcttcactg                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
```
ccaaagtcac tgttccactg                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
tacttgatca gacttcgccc                                               20

<210> SEQ ID NO 24
<211> LENGTH: 24
<212> TYPE: DNA
<213> ORGANISM: Artificial Sequence
<220> FEATURE:
<223> OTHER INFORMATION: Synthetic primer

<400> SEQUENCE: 24
tcctcgtgga gggatttctg ttca                                          24

<210> SEQ ID NO 25
<211> LENGTH: 24
<212> TYPE: DNA
<213> ORGANISM: Artificial Sequence
<220> FEATURE:
<223> OTHER INFORMATION: Synthetic primer

<400> SEQUENCE: 25
ggcagtattg gactccgttc tcat                                          24

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
ggtcctccta ggataggata                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
aacctgaaga gcagtacctg                                               20

<210> SEQ ID NO 28
<211> LENGTH: 21
<212> TYPE: DNA
<213> ORGANISM: Artificial Sequence
<220> FEATURE:
<223> OTHER INFORMATION: Synthetic primer

<400> SEQUENCE: 28
accaacgccg accccaaaca a                                             21

<210> SEQ ID NO 29
<211> LENGTH: 32
<212> TYPE: DNA
<213> ORGANISM: Artificial Sequence
<220> FEATURE:
<223> OTHER INFORMATION: Synthetic primer

<400> SEQUENCE: 29
cttaggaaag actacacgaa tagaggtgcc cc                                    32

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
ataggcatta cgatcgttgg                                                  20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
ggaccaagat ctcctatgaa                                                  20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
cagttccgat gaacagtcac                                                  20

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
tctcgttgta ccgagatgga                                                  20

<210> SEQ ID NO 34
<211> LENGTH: 47
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 34
gtaatacgac tcactatagg gcacgcgtgg tngtcgaswg anawgaa                    47

<210> SEQ ID NO 35
<211> LENGTH: 47
<212> TYPE: DNA

```
<213> ORGANISM: Artificial Sequence
<220> FEATURE:
<223> OTHER INFORMATION: Synthetic primer
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 35
gtaatacgac tcactatagg gcacgcgtgg ttgwgnagsa ncasaga            47

<210> SEQ ID NO 36
<211> LENGTH: 47
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 36
gtaatacgac tcactatagg gcacgcgtgg tagwgnagwa ncawagg            47

<210> SEQ ID NO 37
<211> LENGTH: 47
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 37
gtaatacgac tcactatagg gcacgcgtgg twgtgnagwa ncanaga            47

<210> SEQ ID NO 38
<211> LENGTH: 47
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 38
gtaatacgac tcactatagg gcacgcgtgg tngacgaswg anawgac            47
```

<210> SEQ ID NO 39
<211> LENGTH: 47
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 39
gtaatacgac tcactatagg gcacgcgtgg tncagctwsc tntsctt                    47

<210> SEQ ID NO 40
<211> LENGTH: 22
<212> TYPE: DNA
<213> ORGANISM: Artificial Sequence
<220> FEATURE:
<223> OTHER INFORMATION: Synthetic primer

<400> SEQUENCE: 40
tgtcgcattc ctaccactgc tt                                              22

<210> SEQ ID NO 41
<211> LENGTH: 34
<212> TYPE: DNA
<213> ORGANISM: Artificial Sequence
<220> FEATURE:
<223> OTHER INFORMATION: Synthetic primer

<400> SEQUENCE: 41
cattggttta gttaagtaat tgcatttccg cttc                                 34

<210> SEQ ID NO 42
<211> LENGTH: 32
<212> TYPE: DNA
<213> ORGANISM: Artificial Sequence
<220> FEATURE:
<223> OTHER INFORMATION: Synthetic primer

<400> SEQUENCE: 42
cctaactagg agacaggtct ggataaaaag ag                                   32

<210> SEQ ID NO 43
<211> LENGTH: 28
<212> TYPE: DNA
<213> ORGANISM: Artificial Sequence
<220> FEATURE:
<223> OTHER INFORMATION: Synthetic primer

<400> SEQUENCE: 43
atgcccttag agaaagaaag tgagccct                                        28

<210> SEQ ID NO 44
<211> LENGTH: 31
<212> TYPE: DNA
<213> ORGANISM: Artificial Sequence
<220> FEATURE:
<223> OTHER INFORMATION: Synthetic primer

<400> SEQUENCE: 44
gatatttgcc tggtccacca gaattccata g                                      31

<210> SEQ ID NO 45
<211> LENGTH: 32
<212> TYPE: DNA
<213> ORGANISM: Artificial Sequence
<220> FEATURE:
<223> OTHER INFORMATION: Synthetic primer

<400> SEQUENCE: 45
gggttcgctt ggactatgct atttctgaat aa                                     32

<210> SEQ ID NO 46
<211> LENGTH: 22
<212> TYPE: DNA
<213> ORGANISM: Artificial Sequence
<220> FEATURE:
<223> OTHER INFORMATION: Synthetic primer

<400> SEQUENCE: 46
gtaatacgac tcactatagg gc                                                22

<210> SEQ ID NO 47
<211> LENGTH: 24
<212> TYPE: DNA
<213> ORGANISM: Artificial Sequence
<220> FEATURE:
<223> OTHER INFORMATION: Synthetic primer

<400> SEQUENCE: 47
agcaagcggt attaaagggc gcag                                              24

<210> SEQ ID NO 48
<211> LENGTH: 35
<212> TYPE: DNA
<213> ORGANISM: Artificial Sequence
<220> FEATURE:
<223> OTHER INFORMATION: Synthetic primer

<400> SEQUENCE: 48
tagagaatct agtacagcta tctacgagac gagaa                                  35

<210> SEQ ID NO 49
<211> LENGTH: 26
<212> TYPE: DNA
<213> ORGANISM: Artificial Sequence
<220> FEATURE:
<223> OTHER INFORMATION: Synthetic primer

<400> SEQUENCE: 49
ctactcactc gatttggaag agctgc                                            26

<210> SEQ ID NO 50
<211> LENGTH: 34
<212> TYPE: DNA
<213> ORGANISM: Artificial Sequence
<220> FEATURE:
<223> OTHER INFORMATION: Synthetic primer

<400> SEQUENCE: 50
gtatgggagt tgaatcataa gtaactccta gacc                                   34

<210> SEQ ID NO 51
<211> LENGTH: 34
<212> TYPE: DNA
<213> ORGANISM: Artificial Sequence
<220> FEATURE:
<223> OTHER INFORMATION: Synthetic primer

<400> SEQUENCE: 51
agctcgtaat gaattggatt cgaaccaata tctc                        34

<210> SEQ ID NO 52
<211> LENGTH: 34
<212> TYPE: DNA
<213> ORGANISM: Artificial Sequence
<220> FEATURE:
<223> OTHER INFORMATION: Synthetic primer

<400> SEQUENCE: 52
accggtctgg aattaggtgt agctatatta caag                        34

<210> SEQ ID NO 53
<211> LENGTH: 33
<212> TYPE: DNA
<213> ORGANISM: Artificial Sequence
<220> FEATURE:
<223> OTHER INFORMATION: Synthetic primer

<400> SEQUENCE: 53
caacgattag agagagtagg gagtaccgtt cat                         33

<210> SEQ ID NO 54
<211> LENGTH: 26
<212> TYPE: DNA
<213> ORGANISM: Artificial Sequence
<220> FEATURE:
<223> OTHER INFORMATION: Synthetic primer

<400> SEQUENCE: 54
catcataggt gttgcagcgt cttgag                                 26

<210> SEQ ID NO 55
<211> LENGTH: 24
<212> TYPE: DNA
<213> ORGANISM: Artificial Sequence
<220> FEATURE:
<223> OTHER INFORMATION: Synthetic primer

<400> SEQUENCE: 55
agggttcgta ttcgggtcac aaca                                   24

<210> SEQ ID NO 56
<211> LENGTH: 24
<212> TYPE: DNA
<213> ORGANISM: Artificial Sequence
<220> FEATURE:
<223> OTHER INFORMATION: Synthetic primer

<400> SEQUENCE: 56
gtgagccatg ccataacttg ccca                                   24

<210> SEQ ID NO 57
<211> LENGTH: 22
<212> TYPE: DNA
<213> ORGANISM: Artificial Sequence
<220> FEATURE:
<223> OTHER INFORMATION: Synthetic primer

<400> SEQUENCE: 57
agcaggcttt cagccgtatc tt                                     22

<210> SEQ ID NO 58
<211> LENGTH: 24
<212> TYPE: DNA
<213> ORGANISM: Artificial Sequence
<220> FEATURE:
<223> OTHER INFORMATION: Synthetic primer

<400> SEQUENCE: 58
tcctcgtgga gggatttctg ttca                                   24

<210> SEQ ID NO 59
<211> LENGTH: 22
<212> TYPE: DNA
<213> ORGANISM: Artificial Sequence
<220> FEATURE:
<223> OTHER INFORMATION: Synthetic primer

<400> SEQUENCE: 59
agctgccctt gcttttcctt ca                                     22

<210> SEQ ID NO 60
<211> LENGTH: 23
<212> TYPE: DNA
<213> ORGANISM: Artificial Sequence
<220> FEATURE:
<223> OTHER INFORMATION: Synthetic primer

<400> SEQUENCE: 60
cttgaatgat gctataaatc tcc                                    23

<210> SEQ ID NO 61
<211> LENGTH: 21
<212> TYPE: DNA
<213> ORGANISM: Artificial Sequence
<220> FEATURE:
<223> OTHER INFORMATION: Synthetic primer

<400> SEQUENCE: 61
actacagaat gtagcgagcc g                                      21

<210> SEQ ID NO 62
<211> LENGTH: 23
<212> TYPE: DNA
<213> ORGANISM: Artificial Sequence
<220> FEATURE:
<223> OTHER INFORMATION: Synthetic primer

<400> SEQUENCE: 62
tctttcctcg gcttcctaca cgg                                    23

<210> SEQ ID NO 63
<211> LENGTH: 27
<212> TYPE: DNA
<213> ORGANISM: Artificial Sequence
<220> FEATURE:
<223> OTHER INFORMATION: Synthetic primer

<400> SEQUENCE: 63
cttgcttccc attgtcattg ccattgt                                27

<210> SEQ ID NO 64
<211> LENGTH: 32
<212> TYPE: DNA
<213> ORGANISM: Artificial Sequence
<220> FEATURE:
<223> OTHER INFORMATION: Synthetic primer

```
<400> SEQUENCE: 64
actggtctag ttaacccaga ggaggaatat ac                                    32

<210> SEQ ID NO 65
<211> LENGTH: 30
<212> TYPE: DNA
<213> ORGANISM: Artificial Sequence
<220> FEATURE:
<223> OTHER INFORMATION: Synthetic primer

<400> SEQUENCE: 65
gaaggaacaa tcctcgtatt gaaaccggtc                                       30

<210> SEQ ID NO 66
<211> LENGTH: 23
<212> TYPE: DNA
<213> ORGANISM: Artificial Sequence
<220> FEATURE:
<223> OTHER INFORMATION: Synthetic primer

<400> SEQUENCE: 66
gaggggtgtt gtgattcagc tcc                                              23

<210> SEQ ID NO 67
<211> LENGTH: 20
<212> TYPE: DNA
<213> ORGANISM: Artificial Sequence
<220> FEATURE:
<223> OTHER INFORMATION: Synthetic primer

<400> SEQUENCE: 67
agggtatgat accctttagc                                                  20

<210> SEQ ID NO 68
<211> LENGTH: 20
<212> TYPE: DNA
<213> ORGANISM: Artificial Sequence
<220> FEATURE:
<223> OTHER INFORMATION: Synthetic primer

<400> SEQUENCE: 68
gagatcgtag aaacatgagc                                                  20

<210> SEQ ID NO 69
<211> LENGTH: 20
<212> TYPE: DNA
<213> ORGANISM: Artificial Sequence
<220> FEATURE:
<223> OTHER INFORMATION: Synthetic primer

<400> SEQUENCE: 69
atggcaaatc tggtccgatg                                                  20

<210> SEQ ID NO 70
<211> LENGTH: 27
<212> TYPE: DNA
<213> ORGANISM: Artificial Sequence
<220> FEATURE:
<223> OTHER INFORMATION: Synthetic primer

<400> SEQUENCE: 70
aggggtggga tatttgcctg gtccacc                                          27

<210> SEQ ID NO 71
```

```
<210> SEQ ID NO 71
<211> LENGTH: 20
<212> TYPE: DNA
<213> ORGANISM: Artificial Sequence
<220> FEATURE:
<223> OTHER INFORMATION: Synthetic primer

<400> SEQUENCE: 71
caaataggaa agtggagggt                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic primer

<400> SEQUENCE: 72
cgtatgacgt ctcagtctgt                                              20

<210> SEQ ID NO 73
<211> LENGTH: 20
<212> TYPE: DNA
<213> ORGANISM: Artificial Sequence
<220> FEATURE:
<223> OTHER INFORMATION: Synthetic primer

<400> SEQUENCE: 73
gcctgaacct ataggttcgt                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic primer

<400> SEQUENCE: 74
ttacggccta aatgctgaac                                              20

<210> SEQ ID NO 75
<211> LENGTH: 36
<212> TYPE: PRT
<213> ORGANISM: Arabidopsis thaliana

<400> SEQUENCE: 75

Met Phe Lys Gln Ala Ser Arg Leu Leu Ser Arg Ser Val Ala Ala Ala
1               5                  10                  15

Ser Ser Lys Ser Val Thr Thr Arg Ala Phe Ser Thr Glu Leu Pro Ser
            20                  25                  30

Thr Leu Asp Ser
        35

<210> SEQ ID NO 76
<211> LENGTH: 95
<212> TYPE: PRT
<213> ORGANISM: Oryza sativa

<400> SEQUENCE: 76

Met Ala Ala Arg Arg Ala Ala Ser Ser Leu Leu Ser Arg Gly Leu Ile
1               5                  10                  15

Ala Arg Pro Ser Ala Ala Ser Ser Thr Gly Asp Ser Ala Ile Leu Gly
            20                  25                  30

Ala Gly Ser Ala Arg Gly Phe Leu Pro Gly Ser Leu His Arg Phe Ser
        35                  40                  45
```

```
Ala Ala Pro Ala Ala Ala Thr Ala Ala Thr Glu Glu Pro Ile
        50                  55                  60

Gln Pro Pro Val Asp Val Lys Tyr Thr Lys Leu Ile Asn Gly Asn
 65                  70                  75                  80

Phe Val Asp Ala Ala Ser Gly Lys Thr Phe Ala Thr Val Asp Pro
                 85                  90                  95

<210> SEQ ID NO 77
<211> LENGTH: 54
<212> TYPE: PRT
<213> ORGANISM: Pisum sativum

<400> SEQUENCE: 77

Met Trp Arg Arg Leu Phe Thr Ser Pro His Leu Lys Thr Leu Ser Ser
 1               5                  10                  15

Ser Ser Leu Ser Arg Pro Arg Ser Ala Val Ala Gly Ile Arg Cys Val
                20                  25                  30

Asp Leu Ser Arg His Val Ala Thr Gln Ser Ala Ala Ser Val Lys Lys
            35                  40                  45

Arg Val Glu Asp Val Val
        50

<210> SEQ ID NO 78
<211> LENGTH: 499
<212> TYPE: DNA
<213> ORGANISM: Oryza sativa

<400> SEQUENCE: 78
tttgtattta cttgaatgat gctataaatc tccatcaaaa tgagtaattt cataattgaa      60
taaaaacgag gagccgaaga ttttagggc gggacaaacg cggaagtgta ttgcgttaca     120
aaaaatgaca actagcattt gttttttcat ttcatgttcg aattcgtttt tcgttggaaa     180
aaccaacgcc gaccccaaac aagtctctcc aatataagga gagcggagct taaaaatatt     240
attttattgt gctatggcaa atctggtccg atggctcttc tccactaccc gagggactaa     300
cggtcttcca tatttcatct tcggtgtcgt tgtaggaggc gccctgttgt ttgcttttgct    360 aaagtatcag gcccctctgt acgacccggc tttaatggaa aaaatcatag atcataatat     420
aaaagccggg caccctatag aggttgacta ttcgtggtgg ggcacctcta ttcgtgtagt     480
ctttcctaag taagaaaga                                                  499

<210> SEQ ID NO 79
<211> LENGTH: 27
<212> TYPE: DNA
<213> ORGANISM: Oryza sativa

<400> SEQUENCE: 79
agactacacg aatagaggtg cccccac                                          27

<210> SEQ ID NO 80
<211> LENGTH: 42
<212> TYPE: DNA
<213> ORGANISM: Oryza sativa

<400> SEQUENCE: 80
agactacacg aatagaggtg cccccacttg aataaaaagc at                         42

<210> SEQ ID NO 81
<211> LENGTH: 28
```

```
<212> TYPE: DNA
<213> ORGANISM: Oryza sativa

<400> SEQUENCE: 81
aggttgcccc cacttgaata aaaagcat                                              28
```